US012575891B2

(12) United States Patent
Rafii-Tari et al.

(10) Patent No.: US 12,575,891 B2
(45) Date of Patent: Mar. 17, 2026

(54) AI-BASED AUTOMATIC TOOL PRESENCE AND WORKFLOW/PHASE/ACTIVITY RECOGNITION

(71) Applicant: AURIS HEALTH, INC., Santa Clara, CA (US)

(72) Inventors: Hedyeh Rafii-Tari, Mountain View, CA (US); Menglong Ye, Mountain View, CA (US); Mingyi Zheng, San Jose, CA (US)

(73) Assignee: Auris Health, Inc., Santa Clara, CA (US)

( * ) Notice: Subject to any disclaimer, the term of this patent is extended or adjusted under 35 U.S.C. 154(b) by 856 days.

(21) Appl. No.: 17/533,021

(22) Filed: Nov. 22, 2021

(65) Prior Publication Data

US 2022/0160433 A1 May 26, 2022

Related U.S. Application Data

(60) Provisional application No. 63/244,224, filed on Sep. 14, 2021, provisional application No. 63/156,251, (Continued)

(51) Int. Cl.
*A61B 34/20* (2016.01)
*A61B 17/29* (2006.01)
(Continued)

(52) U.S. Cl.
CPC .............. *A61B 34/20* (2016.02); *A61B 17/29* (2013.01); *A61B 17/3403* (2013.01);
(Continued)

(58) Field of Classification Search
CPC ..... A61B 34/20; A61B 17/29; A61B 17/3403; A61B 90/90; A61B 90/92;
(Continued)

(56) References Cited

U.S. PATENT DOCUMENTS 12,093,813 B2 * 9/2024 Yao .......................... G06N 3/08
2020/0226751 A1 * 7/2020 Jin ......................... A61B 90/37
(Continued)

FOREIGN PATENT DOCUMENTS

WO      WO-2017205373 A1 * 11/2017   ......... A61B 1/00172

OTHER PUBLICATIONS

Namazi, Babak, Ganesh Sankaranarayanan, and Venkat Devarajan. "LapTool-Net: a contextual detector of surgical tools in laparoscopic videos based on recurrent convolutional neural networks." arXiv preprint arXiv:1905.08983 (2019). (Year: 2019).*
(Continued)

*Primary Examiner* — Andrae S Allison
(74) *Attorney, Agent, or Firm* — Paradice & Li LLP

(57) ABSTRACT

A robotic system is configured to automatically identify surgical instruments used during a bronchoscopy procedure. The robotic system can include a video capture device, a robotic manipulator, sensors configured to detect a configuration of the robotic manipulator, and control circuitry communicatively coupled to the robotic manipulator. The control circuitry is configured to perform, using a machine learning classifier, a first analysis of a bronchoscopy video of a patient site to track a medical instrument in the bronchoscopy video. The control circuitry can then identify a set of possible instrument identifications for the medical instrument in the bronchoscopy video based on the first analysis and an identified phase of the bronchoscopy procedure. The control circuitry can then track a motion of the medical instrument in the bronchoscopy video and select an identification from the set of possible instrument identifications for the medical instrument based at least on the tracked motion.

19 Claims, 13 Drawing Sheets

Related U.S. Application Data filed on Mar. 3, 2021, provisional application No. 63/116,768, filed on Nov. 20, 2020.

(51) Int. Cl.

| | |
|---|---|
| *A61B 17/34* | (2006.01) |
| *A61B 90/90* | (2016.01) |
| *A61B 90/92* | (2016.01) |
| *G06T 7/00* | (2017.01) |
| *G06T 7/20* | (2017.01) |

(52) U.S. Cl.
CPC ............ *A61B 90/90* (2016.02); *G06T 7/0012* (2013.01); *G06T 7/20* (2013.01); *A61B 2017/2901* (2013.01); *A61B 2034/2065* (2016.02); *A61B 90/92* (2016.02); *G06T 2207/10016* (2013.01); *G06T 2207/20081* (2013.01); *G06T 2207/30061* (2013.01)

(58) Field of Classification Search
CPC .... A61B 2017/2901; A61B 2034/2065; A61B 34/25; A61B 90/98; A61B 2017/00203; A61B 2034/2048; A61B 2034/2051; A61B 2034/2059; A61B 2034/301; A61B 2090/365; A61B 34/30; G06T 7/0012; G06T 7/20; G06T 2207/10016; G06T 2207/20081; G06T 2207/30061; G06T 2207/10068; G06T 2207/20084; G06T 7/11; G06N 3/044; G06N 3/045; G16H 20/40; G16H 30/40; G16H 50/20
See application file for complete search history.

(56) References Cited

U.S. PATENT DOCUMENTS

| | | | | |
|---|---|---|---|---|
| 2020/0273575 A1* | 8/2020 | Wolf | ...................... | A61B 34/37 |
| 2020/0297444 A1* | 9/2020 | Camarillo | .............. | G16H 30/40 |
| 2021/0282892 A1* | 9/2021 | Kim | ...................... | A61B 90/20 |
| 2022/0040855 A1* | 2/2022 | Cha | ........................ | A61B 90/13 |
| 2023/0093555 A1* | 3/2023 | Ayvali | ............ | A61B 1/000094 |
| | | | | 606/1 |
| 2024/0203567 A1* | 6/2024 | Ruiz | .................... | G06T 7/0012 |

OTHER PUBLICATIONS

A. Jin et al., "Tool Detection and Operative Skill Assessment in Surgical Videos Using Region-Based Convolutional Neural Networks," 2018 IEEE Winter Conference on Applications of Computer Vision (WACV), Lake Tahoe, NV, USA, 2018, pp. 691-699, (Year: 2018).*

Namazi, B., Sankaranarayanan, G. & Devarajan, V. A contextual detector of surgical tools in laparoscopic videos using deep learning. Surg Endosc 36, 679-688 (2022). https://doi.org/10.1007/s00464-021-08336-x (Year: 2022).*

0. Zisimopoulos, E. Flouty, I. Luengo, P. Giataganas, J. Nehme, A. Chow, and D. Stoyanov, "Deepphase: surgical phase recognition in cataracts videos," in International Conference on Medical Image Computing and Computer-Assisted Intervention. Springer, 2018, pp. 265-272, 8 pages.

A. Dosovitskiy, L. Beyer, A. Kolesnikov, D. Weissenborn, X. Zhai, T. Unterthiner, M. Dehghani, M. Minderer, G. Heigold, S. Gelly et al., "An image is worth 16x16 words: Transformers for image recognition at scale," arXiv preprint arXiv:2010.11929, 2020, 22 pages.

A. P. Twinanda, "Vision-based approaches for surgical activity recognition using laparoscopic and rbgd videos," Ph.D. dissertation, Strasbourg, 2017.

A. P. Twinanda, S. Shehata, D. Mutter, J. Marescaux, M. De Mathelin, and N. Padoy, "Endonet: a deep architecture for recognition tasks on laparoscopic videos," IEEE transactions on medical imaging, vol. 36, No. I, 2016, 10 pages.

A. Vaswani, N. Shazeer, N. Parmar, J. Uszkoreit, L. Jones, A. N. Gomez, L. Kaiser, and I. Polosukhin, Attention is all you need; in Advances in neural information processing systems, 2017, 15 pages.

A. Zia, A. Hung, I. Essa, and A. Jarc, "Surgical activity recognition in robot-assisted radical prostatectomy using deep learning," in International Conference on Medical Image Computing and ComputerAssisted Intervention. Springer, 2018, pp. 273-280, 8 pages.

C. I. Nwoye, T. Yu, C. Gonzalez, B. Seeliger, P. Mascagni, D. Mutter, J. Marescaux, and N. Padoy, "Rendezvous: Attention mechanisms for the recognition of surgical action triplets in endoscopic videos," arXiv preprint arXiv:2109.03223, 2021, 21 pages.

C. Lea, R. Vidal, A. Reiter, and G.D. Hager, "Temporal convolutional networks: A unified approach to action segmentation," in European Conference on Computer Vision. Springer, 2016, 4 pages.

D. Hendrycks and K. Gimpel, "Gaussian error linear units (gelus)," arXiv preprint arXiv:1606.08415, 2016, 9 pages.

D. Rivoir, S. Bodenstedt, I. Funke, F. von Bechtolsheim, M. Distler, J. Weitz, and S. Speidel, "Rethinking anticipation tasks: Uncertainty aware anticipation of sparse surgical instrument usage for context aware assistance," in International Conference on Medical Image Computing and Computer-Assisted Intervention. Springer, 2020, 15 pages.

F. Lalys, D. Bouget, L. Riffaud, and P. Jannin, "Automatic knowledge-based recognition of low-level tasks in ophthalmological procedures," International journal of computer assisted radiology and surgery, vol. 8, No. 1, 2013, 11 pages.

G. Lecuyer, M. Ragot, N. Martin, L. Launay, and P. Jannin, "Assisted phase and step annotation for surgical videos," International journal of computer assisted radiology and surgery, 2020, 18 pages.

G. Yengera, D. Mutter, J. Marescaux, and N. Padoy, "Less is more: Surgical phase recognition with less annotations through self-supervised pre-training of cnn-lstrn networks," arXiv preprint arXiv:1805.08569, 2018, 15 pages.

I. Funke, S. Bodenstedt, F. Oehme, F. von Bechtolsheim, J. Weitz, and S. Speidel, "Using 3d convolutional neural networks to learn spatiotemporal features for automatic surgical gesture recognition in video," in International Conference on Medical Image Computing and Computer-Assisted Intervention. Springer, 2019, pp. 467-475, 12 pages.

I. Funke, S. T. Mees, J. Weitz, and S. Speidel, "Video-based surgical skill assessment using 3d convolutional neural networks," International journal of computer assisted radiology and surgery, vol. 14, No. 7, 2019, 15 pages.

K. He, X. Zhang, S. Ren, and J. Sun, "Deep residual learning for image recognition," in Proceedings of the IEEE conference on computer vision and pattern recognition, 2016, 9 pages.

K. He, X. Zhang, S. Ren, J. Sun, Identity mappings in deep residual networks; 2016, 16 pages.

L. A. Torre, R. L. Siegel, and A. Jemal, "Lung cancer statistics," Lung cancer and personalized medicine, 2016, 19 pages.

L. Ding and C. Xu, "Tricomet: A hybrid temporal convolutional and recurrent network for video action segmentation," arXiv preprint arXiv:1705.07818, 2017, 10 pages.

L. Maier-Hein, S. S. Vedula, S. Speidel, N. Navab, R. Kikinis, A. Park, M. Eisenmann, H. Feussner, G. Forestier, S. Giannarou et al., "Surgical data science for next-generation interventions," Nature Biomedical Engineering, vol. 1, pp. 691-696, 2017, 10 pages.

M. Mohamed, G. Cesa, T. S. Cohen, and M. Welling, "A data and compute efficient design for limited-resources deep learning," arXiv preprint arXiv:2004.09691, 2020, 8 pages.

N. Padoy, Machine and deep learning for workflow recognition during surgery, Minimally Invasive Therapy & Allied Technologies, vol. 28, No. 2, 2019, 10 pages.

N. Padoy, T. Blum, S.-A. Ahmadi, H. Feussner, M.-0. Berger, and N. Navab, "Statistical modeling and recognition of surgical workflow," Medical image analysis, vol. 16, 2012, 22 pages.

(56)　　　　　References Cited

OTHER PUBLICATIONS

P. Lei and S. Todorovic, Temporal deformable residual networks for action segmentation in videos; in Proceedings of the IEEE conference on computer vision and pattern recognition, 2018, 10 pages.

S. D. Murgu, "Robotic assisted-bronchoscopy: technical tips and lessons learned from the initial experience with sampling peripheral lung lesions," BMC pulmonary medicine, vol. 19, No. I, 2019, 8 pages.

S. Hochreiter and J. Schmidhuber, "Long short-term memory," Neural computation, vol. 9, No. 8, 1997, 31 pages.

T. Czempiel, M. Paschali, M. Keicher, W. Simson, H. Feussner, S. T. Kim, and N. Navab, "Tecno: Surgical phase recognition with multistage temporal convolutional networks," in International Conference on Medical Image Computing and Computer-Assisted Intervention. Springer, 2020, 10 pages.

X. Gao, Y. Jin, Y. Long, Q. Dou, and P.-A. Heng, "Trans-svnet: Accurate phase recognition from surgical videos via hybrid embedding aggregation transformer," arXiv preprint arXiv:2103.09712, 2021, 13 pages.

Y. A. Farha and J. Gall, "Ms-ten: Multi-stage temporal convolutional network for action segmentation," in Proceedings of the IEEEICVF Conference on Computer Vision and Pattern Recognition, 2019, 10 pages.

Y. Jin, H. Li, Q. Dou, H. Chen, J. Qin, C.-W. Fu, and P.-A. Heng, "Multi-task recurrent convolutional network with correlation loss for surgical video analysis," Medical image analysis, vol. 59, 2020, 31 pages.

Y. Jin, Q. Dou, H. Chen, L. Yu, J. Qin, C.-W. Fu, and P.-A. Heng, "Svrcnet: workflow recognition from surgical videos using recurrent convolutional network," IEEE transactions on medical imaging, vol. 37, No. 5, 2017, 13 pages.

Y. Qin, S. A. Pedram, S. Feyzabadi, M. Allan, A. J. McLeod, J. W. Burdick, and M. Azizian, "Temporal segmentation of surgical subtasks through deep learning with multiple data sources," in 2020 IEEE International Conference on Robotics and Automation (ICRA). IEEE, 2020, 12 pages.

Mingyi Zheng, Menglong Ye, Hedyeh Rafii-Tari, Automatic Biopsy Tool Presence and Episode Recognition in Robotic Bronchoscopy Using a Multi-Task Vision Transformer Network, IEEE—International Conference on Robotics and Automation (ICRA), May 23-27, 2022, 7 pages.

Sharghi et al., "Automatic Operating Room Surgical Activity Recognition for Robot-Assisted Surgery," arXiv:2006.16166v1 [cs.CV] Jun. 29, 2020, 10 pages.

* cited by examiner

AI-BASED AUTOMATIC TOOL PRESENCE AND WORKFLOW/PHASE/ACTIVITY RECOGNITION

CROSS-REFERENCE TO RELATED APPLICATIONS

This application claims priority to U.S. Provisional Application No. 63/116,768, filed on Nov. 20, 2020, U.S. Provisional Application No. 63/156,251, filed on Mar. 3, 2021, and U.S. Provisional Application No. 63/244,224, filed on Sep. 14, 2021, which are herein incorporated by reference in their entireties.

BACKGROUND

Various medical procedures involve recording videos of the procedure, during which of one or more medical instruments are configured to penetrate the human anatomy to reach a treatment site. Certain operational processes can involve inserting the one or more medical instruments through the skin or an orifice of a patient to reach the treatment site, such as performing bronchoscopy to inspect or treat the lungs of the patient. The videos can be analyzed to obtain data about the procedure.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIGS. 5A-1 and 5A-2 (collectively "FIG. 5A"), illustrate a combination of a Multi-task Architecture (MTA) for tool and phase recognition, and a Multi-stage Temporal Convolutional Network (MS-TCN) usable by the automated tool detection system, according to certain embodiments. FIG. 5A-1 shows the left-most portion of the MTA and MS-TCN which extends to the right into FIG. 5A-2. FIG. 5A-2 shows the right-most portion of the MTA and MS-TCN.

DETAILED DESCRIPTION

Figure 1:
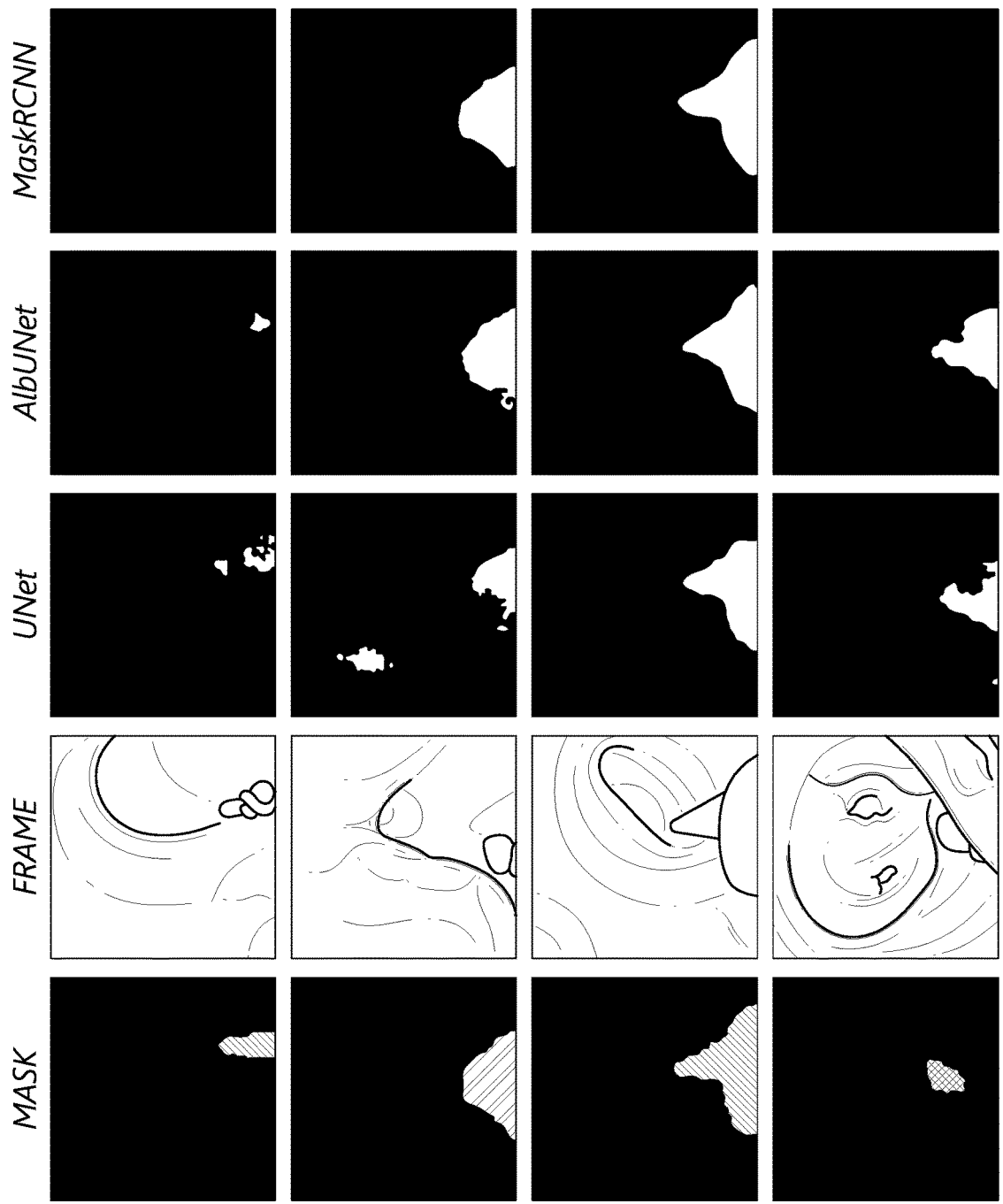
FIG. 1 illustrates an example of tool-presence detection using binary segmentation using different deep learning models, according to certain embodiments.

The headings provided herein are for convenience only and do not necessarily affect the scope or meaning of disclosure. Although certain preferred embodiments and examples are disclosed below, the subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

A workflow recognition system can provide automatic recognition of phases, activities, and workflow in bronchoscopic procedures through recognition of different biopsy tools and instruments (e.g., radial probe endobronchial ultrasound (REBUS), forceps, needle/brush, etc.) and their associated phase from bronchoscope videos.

Automatic recognition of activities and workflow can have significant applications in post-processing of procedures for generating statistics of tools usage, procedure summaries and reports, extracting metrics of skill, and automatic indexing of surgical videos to allow for automated video browsing of certain phases of the procedure. These can be important for training, archiving, and patient-monitoring purposes as well as postoperative review. These methods can also be applied for real-time recognition of activities during the procedure, used towards making real-time recommendations to improve the outcome of a procedure.

Currently, for robotic endoscopic/bronchoscopic procedures, there is no existing solution for obtaining information on tool usage and user behaviors in an automatic way. All post-procedure analysis including examining of events that occur during a certain phase (such as biopsy) is done manually. Likewise, intra-operatively, there is no mechanism in place for automatic recognition of the different phases of the procedure (navigation vs targeting) and what tool is being used.

Automatic AI-based recognition of surgical workflow is a growing area of interest with significant potential to become part of context-aware decision support systems in future enhanced operating room (ORs) and clinical suites, for post-operative analysis, intra-operative monitoring of procedures, and providing automated assistance to the clinical staff.

The workflow recognition system can identify various surgical tools and/or corresponding surgical phases or activities. Tool presence detection and by extension phase/activity recognition from bronchoscopy videos can happen at a frame level or at sequence level of the video. For example, still images in individual frames of a video or sets of frames (e.g., a video clip), including captured motion of the video, can be analyzed.

At the frame level, every frame or a subset of frames of a bronchoscopic video can be classified individually as belonging to a class/category (e.g. REBUS, needle, forceps, etc.). Machine learning approaches can be employed to perform such a classification. In one embodiment, a standard pipeline for achieving this classification includes explicit visual feature extraction on the image, followed by classification with dedicated classifiers that have been previously trained. A classifier may be any algorithm that sorts data into labeled classes, or categories of information. An example is an image recognition classifier to label an image (e.g., "needle," "brush," "forceps," etc.). Classifier algorithms are trained using labeled data. For instance, an image recognition classifier receives training data that labels images. After sufficient training, the classifier then can receive unlabeled images as inputs and will output classification labels for each image. Classifiers can be decision trees, random forests, or support vector machines. However more recent deep-learning based models that rely on Convolutional Neural Networks (CNNs) are more promising, and can be used for both image/tool segmentation and tool classification. Example of CNN-based architectures that can be used for this task include ResNet, U-Net and MaskRCNN, among others.

While the following provides examples of specific machine algorithms performing automated tool recognition and associated functions, these functions may be performed by different machine algorithms that provide similar functionality. The naming of specific machine algorithms below are not meant to imply that only those machine learning algorithms can be used. The techniques described below may be used with other machine learning algorithms to provide automated tool recognition.

Machine Learning Algorithms

FIG. 1 illustrates an example of tool-presence detection using binary segmentation using different deep learning models, according to certain embodiments. In binary segmentation, binary images are produced from color images by segmentation. Segmentation is the process of assigning each pixel in the source image to two or more classes. For example, one type of segmentation assigns pixels to either the foreground or the background based on grayscale intensity.

As illustrated in FIG. 1, the second "Frame" column includes examples of various frames taken from a bronchoscopy video. These frames are processed using various machine learning algorithms (e.g., UNet in column 3, AlbU-Net in column 4, and MaskRCNN in column 5) to perform binary segmentation and generate a mask, as shown in the first "Mask" column, identifying the portions of the image comprising the instrument. In some embodiments, results from the various machine learning algorithms may be combined to generate the mask. In some cases, particular machine learning algorithms may be better at identifying certain types of instruments. Therefore, alternatively, results from one machine learning algorithm may be selected for the mask depending on the type of instrument suspected of being in the video. In some embodiments, supplemental data such as data collected by a robotic system, can be used to narrow down the possible identifications for a medical instrument. In these situations, it may be possible to put more weight on results from machine algorithms that are better at identifying those types of instruments (e.g., by using a weighted average) or otherwise prioritizing the output from a particular machine algorithm in determining the final mask for the frame.

Figure 2:
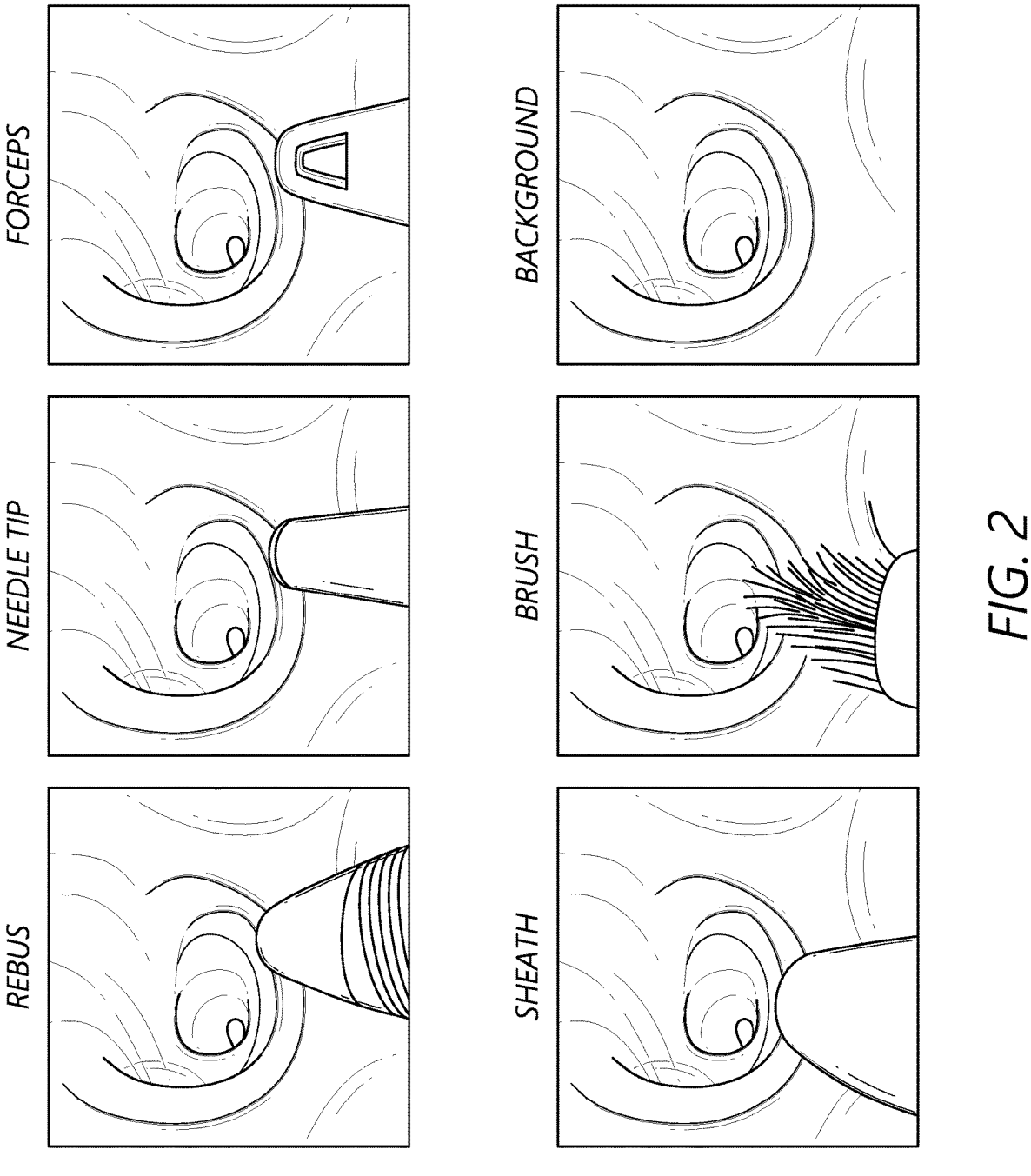
FIG. 2 illustrates an example of the classification of an image frame into different sub-classes corresponding to various medical instruments, according to certain embodiments.
Figure 8:
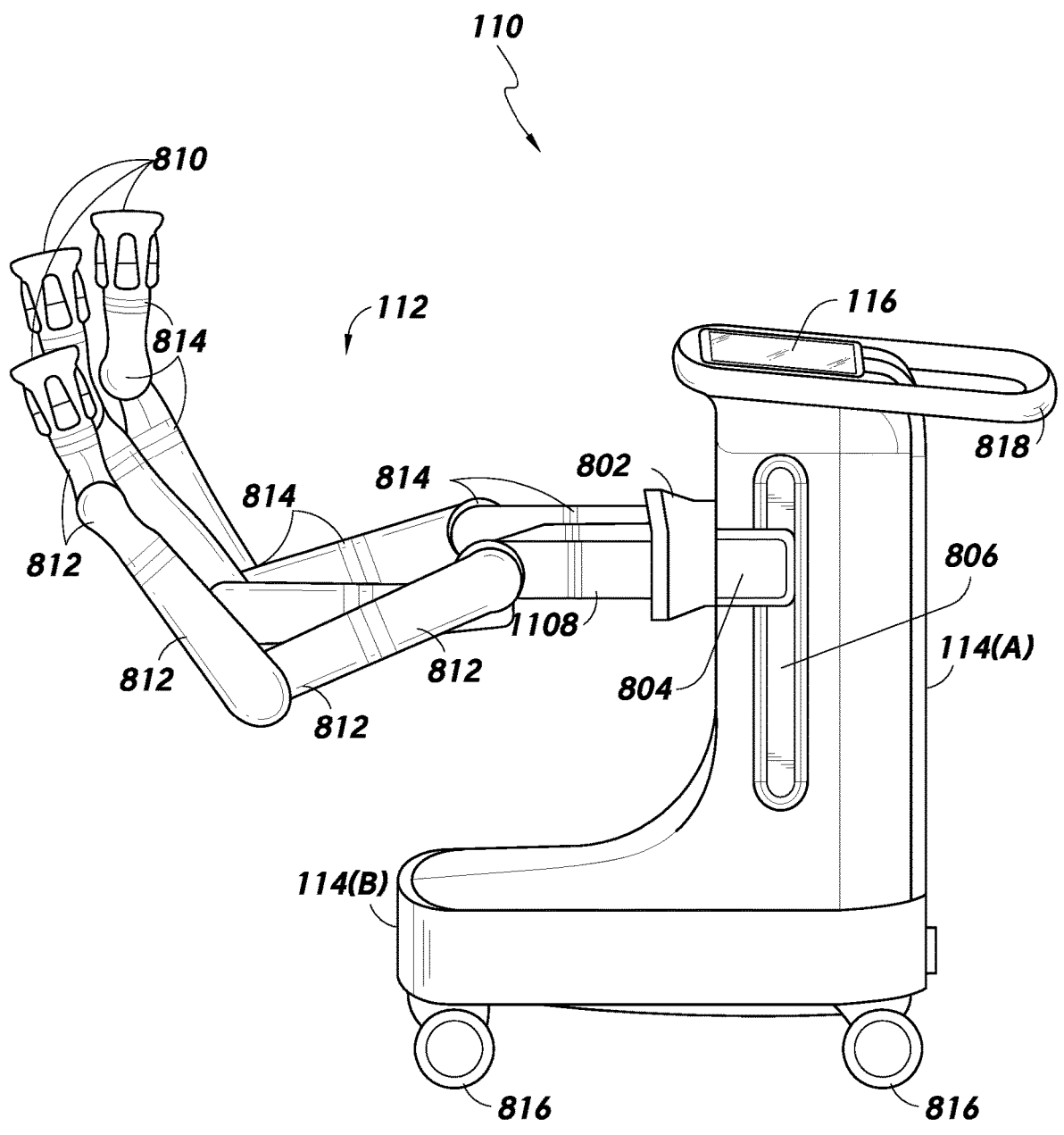
FIG. 8 illustrates example details of a robotic system that can incorporate the automated tool detection system, according to certain embodiments.

FIG. 2 illustrates an example of the classification of an image frame into different sub-classes corresponding to various medical instruments, according to certain embodiments. After identifying the portion of the image associated with the medical instrument, additional image processing can be performed (e.g., using machine learning algorithms, selection criteria, etc.) to identify the medical instrument. Supplemental data from the robotic system (e.g., as shown in FIG. 8) performing a medical procedure, such as bronchoscopy, can be used to aid in instrument identification. Such supplemental data can include phase information for the procedure, which can be used to narrow down the possible medical instruments based on knowledge of the typical instruments used during particular phases of the bronchoscopy procedure. For example, during a targeting phase and biopsy phase, the instruments likely used are REBUS, needle, brush, and forceps. If the bronchoscopy procedure is in those phases, then the possible choices for the instrument identification for the instrument recorded in a video can be narrowed down to those possibilities.

Furthermore, there may be additional supplemental data available from the robotic system that can further narrow down the possible medical instrument. For example, sensors in the robotic system may be able to identify the motions imparted on the medical instrument being manipulated by the robotic system. In addition, video of the medical procedure (e.g., bronchoscopy video captured by an endoscope) can be analyzed to identify the motion of the medical instrument tracked in the video frames.

In one example, the REBUS instrument can be identified by looking for a specific motion. A REBUS instrument is typically used to get confirmation of a nodule location. One type of REBUS has a tip of that is silver with ridges. The ridges may form a spiral or screw around the surface. During use, movement of the REBUS can include rotation. This rotation is captured across several frames of the video and can be identified in the video, for example, by tracking the movement of the ridges. This rotation motion can be used to identify a tracked medical instrument used during the targeting/biopsy phase as a REBUS.

In another example, a needle or brush can be identified by looking for a specific motion. The needle and brush are typically used to get a biopsy sample once a nodule is localized. During sampling, the needle or brush typically moves in a back and forth dithering motion. This dithering motion can be used to identify a tracked medical instrument used during the targeting/biopsy phase as a needle or brush. In addition, certain medical instruments used with the robotic system may use a particular coloring for the medical instrument. One type of needle has a gold tip and/or a milky white sheath. Either or both these colorations can be used to identify a tracked medical instrument as a needle. Other manufacturers may use a different color. For example, needles from another manufacturer may use a blue sheath.

In another example, the forceps can be identified by looking for a specific motion. The motion can include a quick and hard pull motion, as the forceps are used to pull a sample from lung tissue. This pulling motion can be used to identify a tracked medical instrument used during the targeting/biopsy phase as forceps.

Different classes and sub-classes can be defined for this classification process. Classes and sub-classes may range from more general classification to more detailed classifications. For example, more general classifications of images or portions of images can include background, REBUS, needle, forceps. More detailed or granular classifications (e.g. sub-classes) can include first-party manufacturer sheath, third-party manufacturer sheath, needle tip, forceps tip, brush tip, etc.

In some embodiments, class identification comprises a tool-presence detection step and an episode recognition step. During image processing, episodes can be identified in the video. In one embodiment, an episode is a sequence of 8 frames that are labeled by using the class of the majority of the frames across that episode. This operates using an assumption that an episode, in actuality, only has one class within the 8-frame time window and outlier classifications can be ignored. As will be apparent, other numbers of frames can be used to define an episode.

During the tool-presence detection step and the episode recognition step, a tracked medical instrument is identified into one of several classes. In one embodiment, the tool-presence detection step uses four classes and the episode recognition step uses six classes. For example, four classes for tool-presence detection can include REBUS, forceps, brush, needle tip, sheath and background. In another example, the episode recognition step can use the types of motion identified in the frames of the episode to categorize the episode into one of several classes including REBUS-type, forceps-type, needle-type, and background-type. The classes can include several instruments, and a particular instrument can be in multiple classes. In one embodiment, the REBUS-type class can include a REBUS and a sheath. The forceps-type class can include forceps and a needle. The needle-type class can include a needle tip, a brush, and a sheath. The background-type can be a catch-all for various images without a medical instrument (e.g., bronchial passageways or other patient site). As described above, rotational movement can indicate a REBUS instrument, dithering can indicate a needle or brush, and a quick pulling motion can indicate forceps.

Different embodiments may use different types of classifiers or combinations of classifiers. Sequence based models that try to capture the temporal information and sequence of activities in a procedure may be more capable of identifying surgical phase and activity recognition, and can be used at different levels of a procedure (phases/tasks, activities/sub-tasks etc.).

Some embodiments can rely on detecting visual cues in the images, using traditional image processing tools for detecting color, shape, or texture information, and use standard machine learning and statistical analysis methods such as Hidden Markov Models (HMMs) and Dynamic Time Warping (DTW) to capture the temporal information for classification of phases and activities. Some of the above statistical methods rely on whole video sequences and possibly may not work in an online recognition scenario.

Some embodiments rely on neural networks and deep learning-based architectures for both capturing the features of the images and incorporating the temporal information, and can be used both for post-processing of entire video sequences as well as for online recognition, while demonstrating improved recognition and classification performance. These embodiments can use CNNs to extract and capture features of the images, followed by Recurrent Neural Networks (RNNs) such as Long-short term memories (LSTMs), to capture the temporal information and sequential nature of the activities. Temporal Convolutional Networks (TCNs) are another class of more recent architectures that can be used for surgical phase and activity recognition, which can perform more hierarchical predictions and retain memory over the entire procedure (as opposed to LSTMs which retain memory for a limited sequence and process temporal information in a sequential way).

Figure 3:
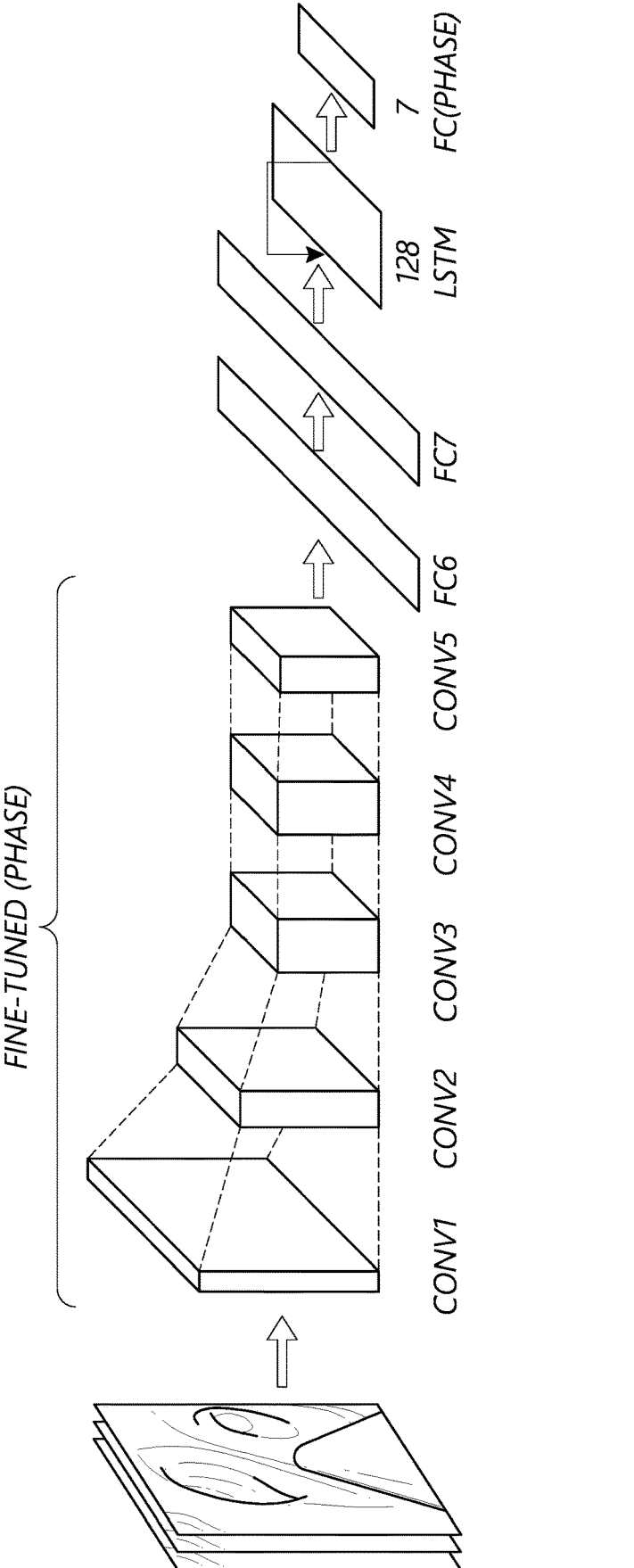
FIG. 3 illustrates a Convolutional Neural Network and Long-Short Term Memories architecture usable by an automated tool detection system, according to certain embodiments.
Figure 4:
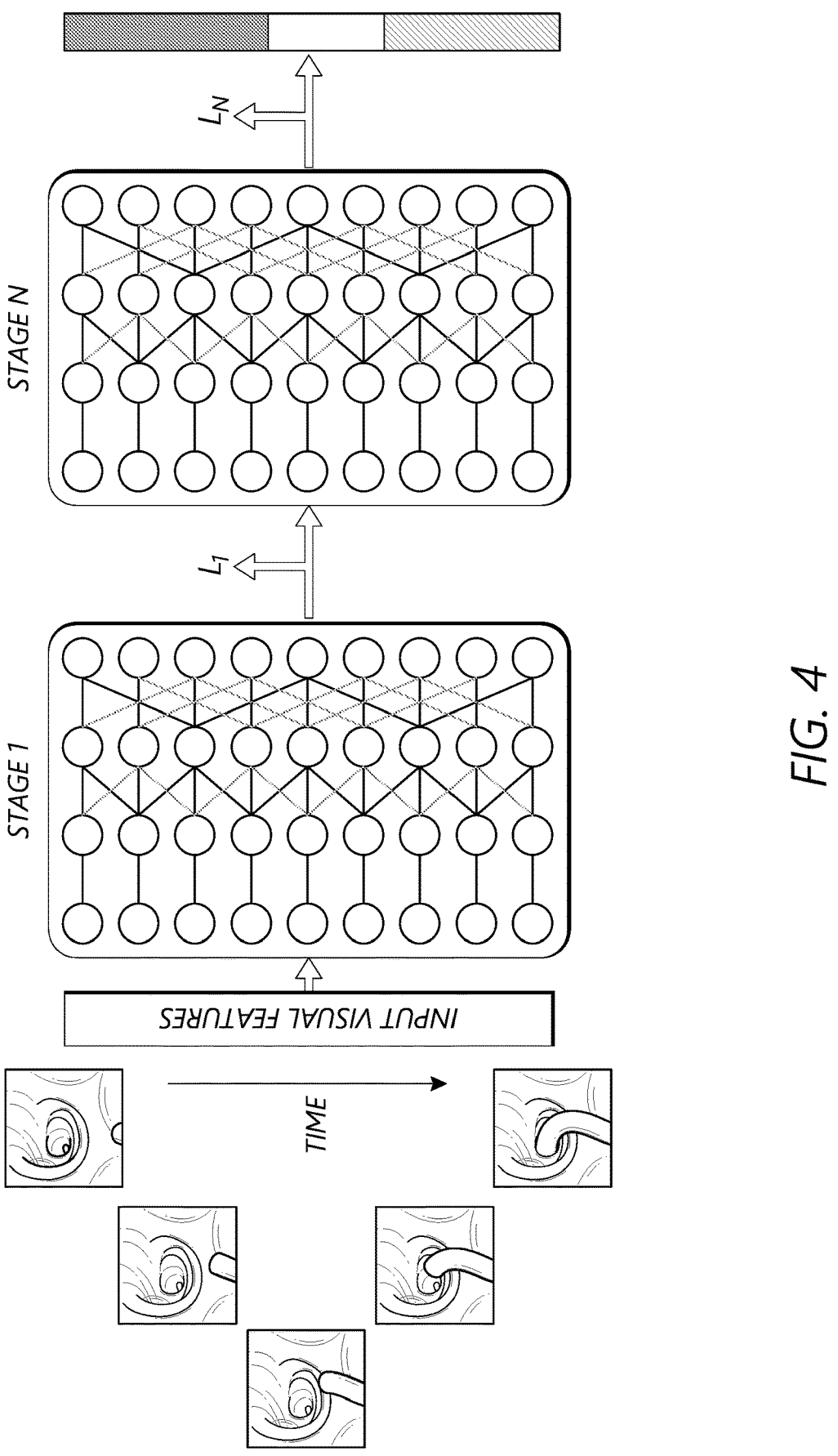
FIG. 4 illustrates a multi-stage Temporal Convolutional Network architecture usable by the automated tool detection system, according to certain embodiments.
Figures 1, 5A:
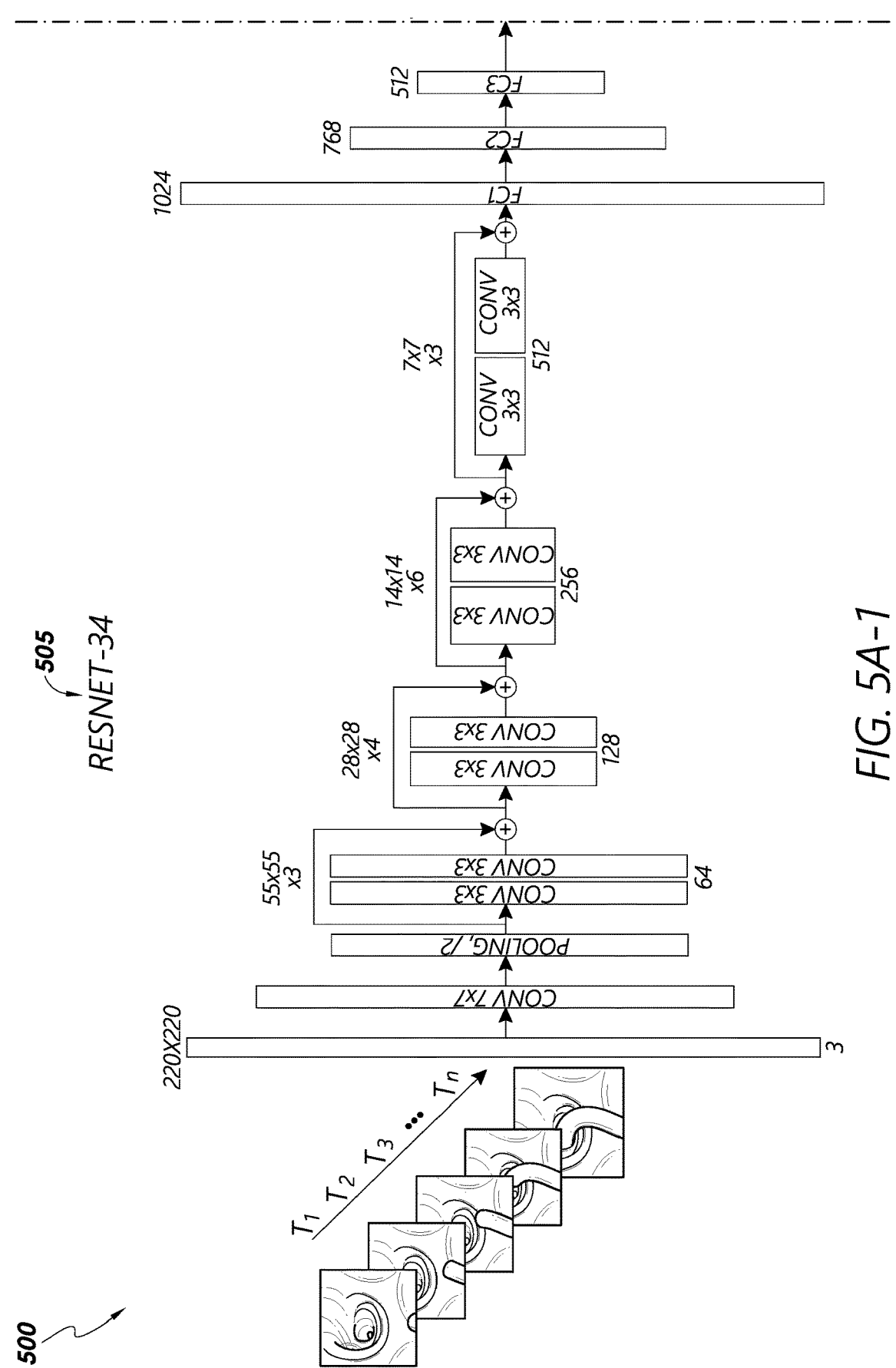
Figures 2, 5A:
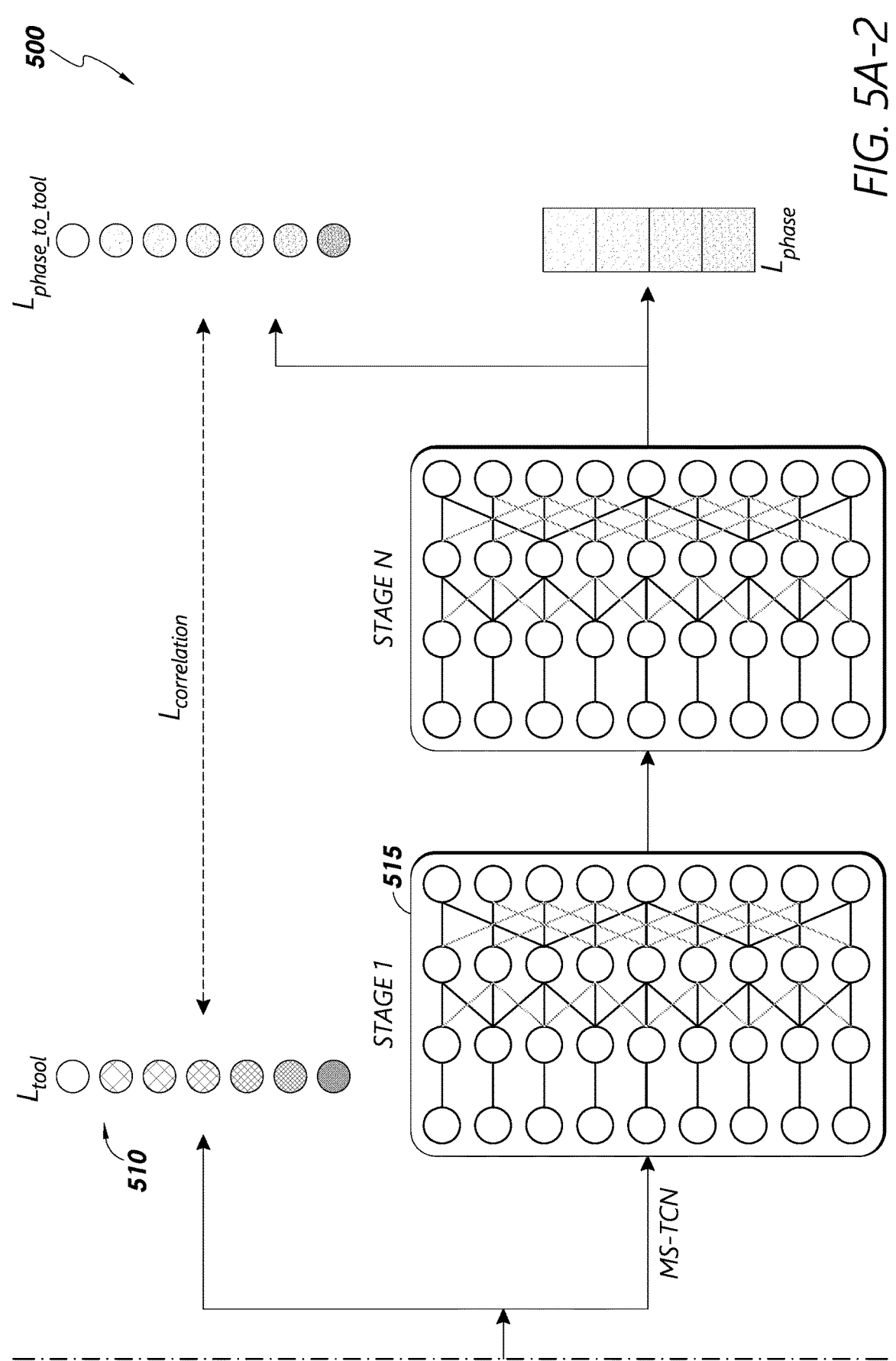

Examples of these deep learning-based architectures applied to bronchoscopic video data for recognition of phases and activities are shown in FIGS. 3-5. These machine learning architectures can be used by an automated tool detection system to identify medical instruments in videos and other image data (e.g., still pictures or video frames). FIG. 3 illustrates a CNN+LSTM architecture while FIG. 4 illustrates a multi-stage TCN architecture.

FIG. 5A, which is split across two sheets as FIGS. 5A-1 and 5A-2, illustrates a combination of a Multi-task Architecture (MTA) 500 for tool and phase recognition, and a Multi-stage Temporal Convolutional Network (MS-TCN) 515. The MTA includes a convolution backbone 505 and two branches 510, 515, which can solve for different tasks in each branch. Data is processed by the earlier convolution backbone 505 and the output of the convolution backbone 505 is shared between the two branches. For example, the convolution backbone 505 may use a ResNet neural network for feature extraction, with the number of layers (e.g., 18, 34, 50, etc.) selected based on the desired tradeoff between performance and complexity. In one embodiment, the backbone 505 includes multiple layers of blocks with skip connection, a dropout layer, a max pooling layer, and several fully connected layers. The blocks can include convolution layers, a batch normalization layer, and a rectified linear unit (ReLU) non-linearity layer. In one embodiment, the output of the shared backbone is a 512-dimension feature vector. Other embodiments of the backbone 505, may have different outputs, such a vector with a different number of dimensions.

One branch 510 of the MTA 500 can use a neural network suited for tool recognition, while the other branch 515 can use a second neural network better suited for phase recognition. Different types of neural networks are better suited for particular tasks. For example, CNNs are better suited for spatial data, such as images, while RNNs networks are better suited for sequential data, such as video and/or audio.

For tool recognition, the Multi-task architecture can use a first neural network 510 such as CNN, while for phase recognition, the MTA 500 can use a second neural network 515, such as MS-TCN or its variations. With the convolutional backbone 505 (e.g. a CNN such as ResNet) being shared in the earlier layers, the first neural network 510 in the tool branch and second neural network 515 in the phase branch can be jointly optimized, for example, through adjustments of the convolution backbone.

As discussed above, TCNs can perform more hierarchical predictions and retain memory over the entire procedure in comparison to some other neural networks. For example, TCNs exhibit longer memory than recurrent architectures with the same capacity. TCNs can also provide better parallelism, flexible receptive field size, stable gradients, low memory requirements for training, and/or variable length inputs.

Using an MS-TCN network for phase recognition can provide certain advantages. For example, using a TCN can reduce computational cost while providing a larger receptive field. Meanwhile, using a multi-stage stack for the TCN can improve the prediction. For example, the MTA 500 using MS-TCN can obtain phase classification accuracy for certain surgical tools from 83% to 99%. In comparison, other neural network architectures may perform several % points worse, depending on the surgical tool/phase.

Multi-stage TCNs, are constructed by stacking multiple TCNs so that the output from pervious stage passes to the next stage with dilated convolutions. Compared to recurrent neural networks such as LSTMs, TCNs have a larger receptive field due to the dilation convolution layer and in order to extend the temporal length of the input sequence. Thus, TCNs are able to obtain more abundant dynamic information than LSTMs with the same amount of computing power. On the other hand, the cascading multi-stage design with higher temporal resolution further refines prediction during phase transitions.

Correlation loss can be calculated between the two branches to minimize the divergence of the prediction between the two branches. This mechanism penalizes the model when the correlated tasks result in conflicting predictions.

In one embodiment, cross entropy loss can be used for both branches, tool-presence detection and phase recognition, since both are multi-class problem. Denoting the input video clip by E, and the frame at certain timestamp t of the video as $f_t$, where $t \in [1; T]$ and T is the total frame number. Each E consists of a number of frames N, and $f_{t:t+N}$. The cross entropy loss for tool-presence detection for each video clip may be defined as:

$$L_T(g_t, p_t) = -\sum_i^N \sum_j^{C_t} g_{t(i,j)} \log p_{t(i,j)}$$

where $g_t$ is the ground truth of tools and $p_t$ is the predicted probability from tool-presence detection branch. $C_t$ is the total number of tool classes. Both $g_t$ and $p_t$ have a dimension of $N \times C_t$.

In one embodiment, the cross entropy for phase recognition may be:

$$L_E(g_e, p_e) = -\sum_i^{C_e} g_{e_i} \log p_{e_i}$$

where $g_e$ is the ground truth of tools and $p_e$ is the predicted probability from the tool-presence detection branch. $C_e$ is the total number of tool classes. Both $g_e$ and $p_e$ have a dimension of $N \times 1$.

In some embodiments, the total loss can be calculated by the summation of the above two cross entropy loss functions. For example, the total loss for the summation of the two branches can be defined as:

$$Loss = L_T(g_t, p_t) + L_E(g_e, p_e)$$

Figure 5B:
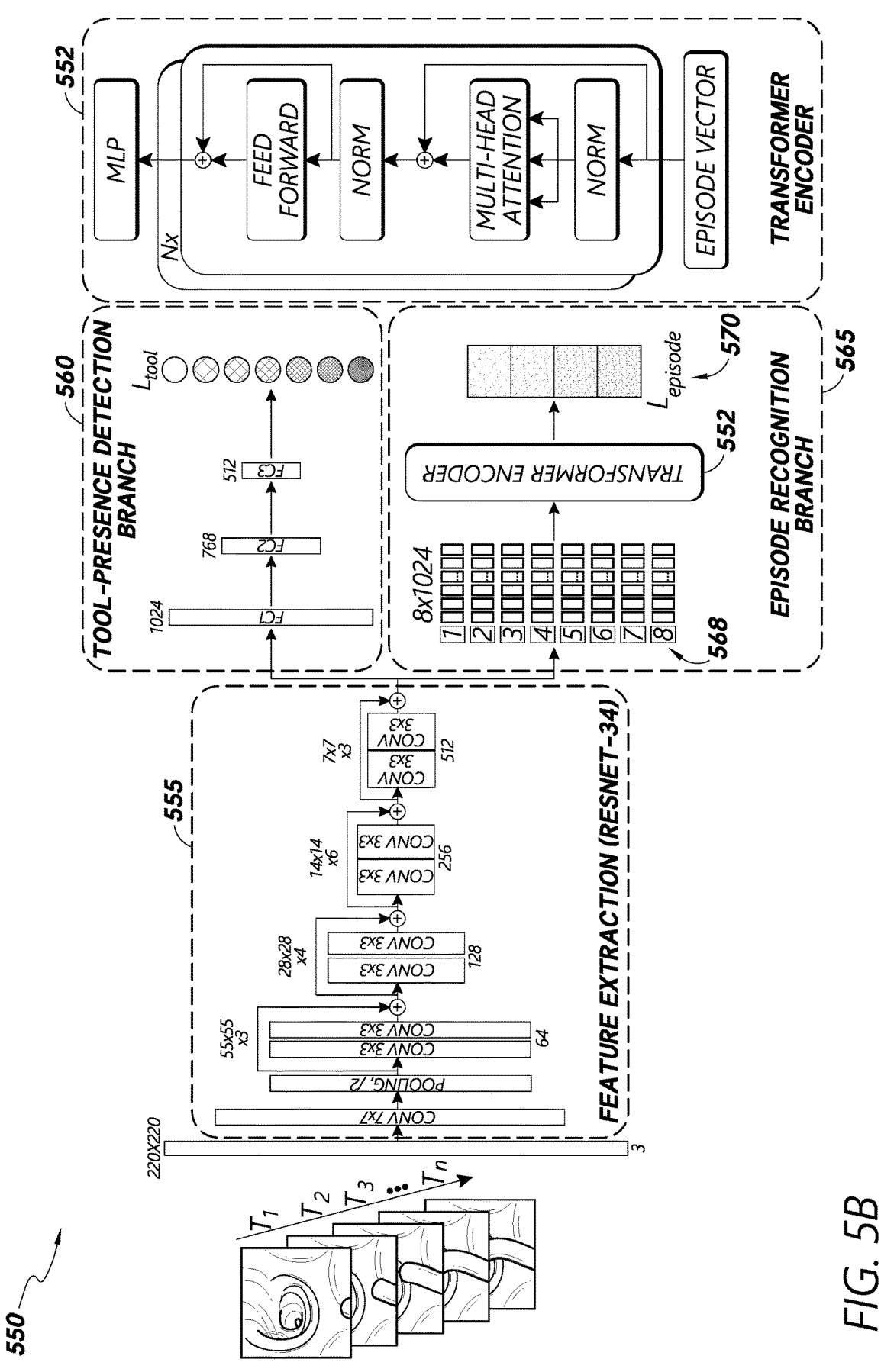
FIG. 5B illustrates a Multi-task Architecture for tool and phase recognition that uses a transformer encoder, according to certain embodiments.

FIG. 5B illustrates a Multi-task Architecture 550 for tool and phase recognition, similar to the MTA architecture described in FIG. 5A, with the addition of a transformer encoder 552. The MTA includes a convolution backbone 555 (e.g., ResNet) and two branches, a tool-presence detection branch 560 and an episode recognition branch 565, which can solve for different tasks in each branch. Data is processed by the earlier convolution backbone 555 and the output of the convolution backbone 555 is shared between the two branches. For example, the convolution backbone 555 may use a ResNet neural network for feature extraction, with the number of layers (e.g., 18, 34, 50, etc.) selected based on the desired tradeoff between performance and complexity. In one embodiment, the backbone 555 includes multiple layers of blocks with skip connection, a dropout layer, a max pooling layer, and several fully connected layers. The blocks can include convolution layers, a batch normalization layer, and a rectified linear unit (ReLU) non-linearity layer. In one embodiment, the output of the shared backbone is a 512-dimension feature vector. Other embodiments of the backbone 555, may have different outputs, such a vector with a different number of dimensions.

The tool-presence detection branch 560 branch of the MTA 550 can use a neural network suited for tool recognition, while the episode recognition branch 565 can use a second neural network better suited for phase recognition. Different types of neural networks are better suited for particular tasks. For example, CNNs are better suited for spatial data, such as images, while RNNs are better suited for sequential data, such as video and/or audio. Examples of different types of neural networks that can be used for the two branches are described above in FIG. 5A.

A transformer is a model that differentially weights the significance of each part of the input data. Transformers can be used in the field of natural language processing and in computer vision. Transformers are designed to handle sequential input data, such as natural language, for tasks such as translation and text summarization. However, unlike RNNs which also handle sequential input data, transformers do not necessarily process the data in order. Transformers make use of an encoder and a decoder architecture. The encoder consists of encoding layers that process the input iteratively one layer after another, while the decoder consists of decoding layers that do the same thing to the encoder's output. In addition, transformer networks make extensive use of attention mechanisms.

Attention is a technique that mimics cognitive attention, which enhances the important parts of the input data and fades out the rest, such that the neural network devotes more computing power on the important part of the data, which may be a small part of the data. The two most common attention techniques are dot-product attention, which uses the dot product between vectors to determine attention, and multi-head attention, which combines several different attention mechanisms to direct the overall attention of a network or sub-network.

The attention mechanism used in transformers can provide context for any position in the input sequence. The transformer can process a natural language sentence out of order, for example, processing the end of the sentence before the beginning. The transformer can identify the context that confers meaning to each word in the sentence. This feature allows for more parallelization than RNNs and can reduce training times.

A transformer encoder typically has two major components: a self-attention mechanism and a feed-forward neural network. The self-attention mechanism accepts input encodings and weighs their relevance to each other to generate output encodings. The feed-forward neural network further processes each output encoding individually.

The transformer encoder 552 can be used for episode recognition, taking advantage of its properties of a global receptive field and self-attention. The receptive field is the region of the input space that affects a particular unit of the network. Self-attention, also known as intra-attention, is an attention mechanism relating different positions of a single sequence in order to compute a representation of the same sequence. The self-attention model allows inputs to interact with each other (i.e. calculate attention of all other inputs with respect to one input), allowing the interactions to identify which inputs are more important. However, a problem that can occur with a transformer, due to the limited data size in medical applications, is that lack of generalization can lead to poor performance, where generalization refers to a model's ability to classify or forecast new, previously unseen data.

The Vision Transformer (ViT) model is a particular transformer model that can be used in computer vision for image recognition. In ViT, each image is split into a sequence of fixed-size non-overlapping patches. Self-attention mechanisms are then used to find the important patches. In the context of medical applications, dividing an image directly into a number of patches can cause the loss of translation equivalence, which is a property that exists when using convolution network and which can improve generalization in the datasets of limited size. In addition, if patches are too large, the local contextual information of each patch will be lost. If the patch size is too small (resulting in a greater total number of patches), the computation cost grows exponentially. In one embodiment, the episode recognition branch 565 can use ResNet with a transformer encoder 1002 to gain the generalization capability from ResNet while keeping the global receptive field property from using a transformer encoder 552.

In some embodiments, data (e.g., video) is divided into episodes. For example, each episode can be made of a number of video frames (e.g., 8 frames). Each episode can be processed by ResNet (or other machine learning algorithm) to generate an embedded episode vector 568 for transformer encoder 552. For example, the input of the transformer encoder can be an 8×1024 embedded episode feature vector, which solves the model capacity issue of transformer Since the transformer is designed to deal with natural language processing (NLP) problems, the transformer takes the inputs of word embeddings. ResNet includes a vectors feature that allows turning each episode (e.g., 8 frames) into an embedded episode vector for the transformer encoder. For example, the input of transformer encoder 1002 can be an 8×1024 embedded episode feature vector, which may solve the model capacity issue of transformer. Moreover, since the temporal sequence of the frames is naturally positioned in order, the transformer encoder is capable of using temporal information to capture rapid tool movement.

As shown in the expanded view of the transformer encoder 552 in FIG. 5B, the transformer encoder 552 can receive as an input, an episode vector, such as that described above. The episode vector is normalized and processed using a multi-head attention (MHA) mechanism. The output of the MHA mechanism is combined with the episode vector and again normalized. The normalized output is then processed by a feed-forward mechanism. The output of the feed-forward mechanism is combined with the normalized output to produce the transformer encoder output. The transformer encoder output may then be used as input to another neural network, such as a multilayer perceptron (MLP) (e.g., Lepisode 570), a class of feedforward artificial neural network.

Surgical Workflow Analysis

One of the possible applications for embodiments of the above system is in the field of surgical workflow recognition, which has multiple post-operative and intra-operative applications and includes the study of surgical phases, activities, tasks, and sub-tasks at different levels of a procedure. The information obtained from these can be used for automatic analysis of surgical videos, post-procedure evaluation, analysis of surgical skill and training purposes, as well as reducing surgical errors and improving real-time communications in the operating room.

Examples of the different phases for a bronchoscopy procedure that can be detected from video image data can include: 1) Preparation, 2) Initialization, 3) Registration, 4) Navigation, 5) Biopsy (also referred to as Targeting). Within the navigation phase, there could be phases corresponding to different initial portions of the procedure where no tool is present in the camera view. For example, the navigation phase may encompass earlier phases such as preparation, initialization, or registration. Within the biopsy (targeting) phase there could be phases corresponding to different instruments and tools such as REBUS, forceps, needles or brushes.

Figure 6:
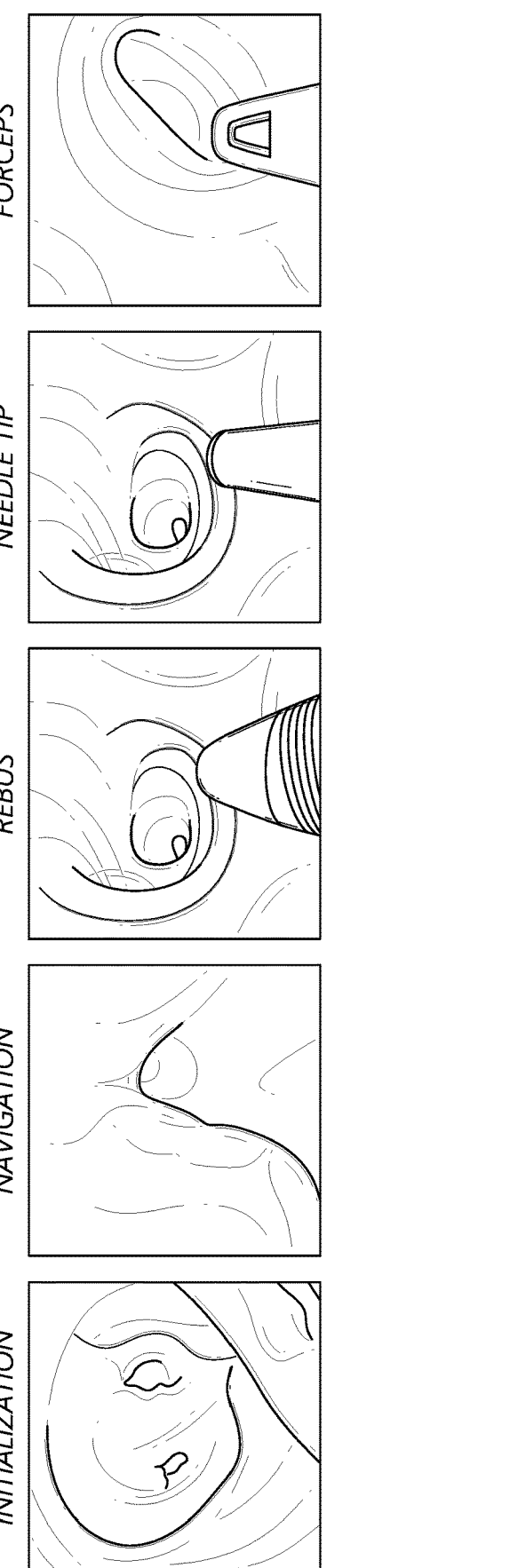
FIG. 6 illustrates an example of identifications made by the automated tool detection system, according to certain embodiments.

An example of these different phases/activities of a bronchoscopy procedure is shown in FIG. 6. FIG. 6 illustrates an example of identifications made by the automated tool detection system, according to certain embodiments. In FIG. 6, during the targeting phase of the bronchoscopy procedure, the following medical instruments are identified: REBUS, needle, and forceps.

Post-Operative Applications

Other possible applications for embodiments of the above system include post-operative processing of the captured data. The following are some of the post-procedure applications and use-cases of the system.

Figure 7:
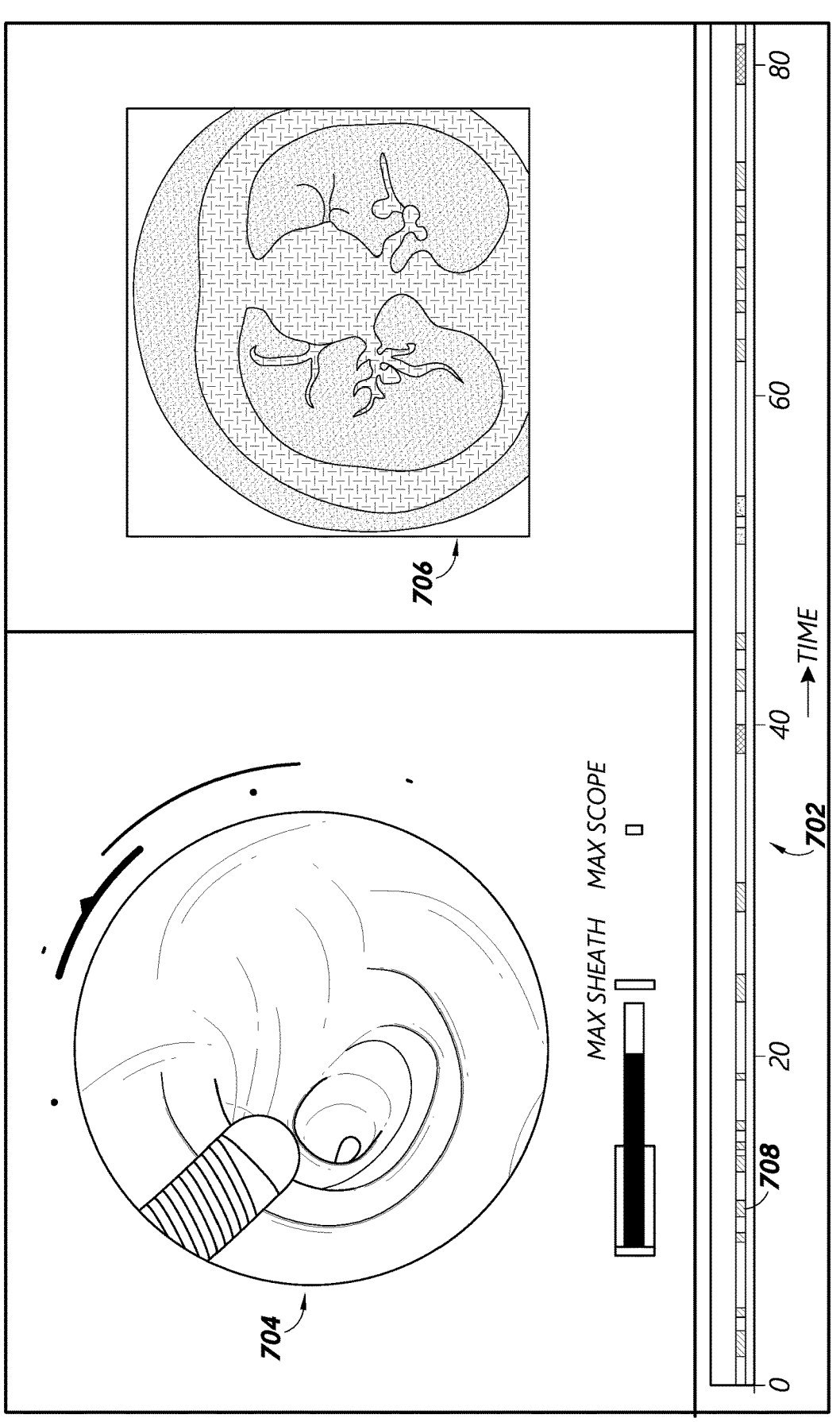
FIG. 7 illustrates a user interface for automated browsing/indexing of videos that utilizes phase recognition, according to certain embodiments.

Automatic Indexing of Videos (Video Analysis/Browsing): The workflow recognition system can automate the indexing of surgical videos. Manual indexing is a time-consuming process. Thus, automatic indexing can allow for easy browsing of phases by automatically navigating to a certain phase of a video or a certain tool. This is particularly useful for training purposes and post-operative review. FIG. 7 shows one such use case, where each color in the bar denotes a phase/activity label, extracted from the video (e.g., Orange-REBUS, Yellow-Needle, Pink-Forceps). By clicking on a certain point on the bar, corresponding to a certain phase or activity (in this case REBUS) the video can automatically go to that part of the procedure to facilitate easier browsing of activities and tool usage and analysis of video of the procedure. Another use case can be automated cropping of certain parts of the video (e.g. biopsy phase) that are of interest to user. For example, during review of a video of a procedure, the system may cause the video to focus on the surgical instrument and/or target location or object.

FIG. 7 illustrates a user interface for automated browsing/indexing of videos that utilizes phase recognition, according to certain embodiments. The user interface may be part of the automated tool detection system. The user interface includes a seek bar 702, a video screen 704, and a procedure overview panel 706. The seek bar 702 indicates the automatically detected activities of a case/procedure with annotations 708 enabling users to directly find the video segment corresponding to a certain activity, for post-procedure analysis. In some embodiments, the annotations 708 may be colored in the seek bar to group segments of the video that are similar. For example, the segments may be grouped by phase, by activity, and/or by instrument. In one embodiment, the annotations 708 are colored to denote a specific instrument. Users can then seek to all annotations of one color (e.g., red) to find instances where that instrument (e.g. needle) was used. In some embodiments, different colors can be used to denote the importance of a particular activity in the procedure.

Generate procedure summaries and reports: The workflow recognition system can generate statistics for the different phases, tool usage, and case times. For example, the system may generate reports or summaries automatically at the end of a procedure. These reports or summaries can include statistics such as: number of biopsy attempts with each of the tools (forceps, needle, first party vs third party instrument usage); amount of time spent using REBUS, needle, forceps, or brush; amount of time spent in each phase (navigation time, targeting/biopsy time, etc.); and/or number of interruptions.

Skill Assessment: The workflow recognition system can generate metrics of skill and how good a physician is at a particular skill. The system may also monitor whether the physician is improving at the skill over time (e.g., usage of the robotic system to perform a bronchoscopic procedure). Skill metrics can be extracted from tool usage, duration of time spent in each of the phases, number of biopsies taken, and different tool occurrences (needle, forceps, brush). Another use case can be extracting patterns of behavior from more experienced operators vs. novice operators, that can then be used for feedback during skill training. The system may also correlate these with procedure outcomes to understand which tools/procedures/behaviors work best in terms of outcomes.

Intra-Operative Application

The workflow recognition system can also be used during operations. For example, the system can be used to recognize phases, activities, and tool presence during an operation.

Real time recommendations: For example, the workflow recognition system can identify phases and tools in real-time and, based on identified phases, make recommendations for which tools to use in the current phase or next phase. The system may also send notifications related to identified tools. The system may make recommendations for which views to use (e.g., selecting between camera feeds or UI output), based on identified phase/tool or change views automatically (e.g. use 3D map and virtual view during Navigation phase, use tip view and bull's eye view during biopsy/targeting phase). The system can provide warnings to the user in case of detected deviations and anomalies during the procedure. In one example, the system can potentially predict the amount of saline needed during a phase of the operation based on the captured image and/or sensor readings.

Real time duration prediction: The workflow recognition system can also be used to provide real time prediction of current phase duration and remaining procedure time based on the identified tools and phases.

Intelligent Guidance/Tool Tracking: The workflow recognition system can also be used to provide intelligent guidance, which can include image-based tool detection, tool pose estimation or tracking of the different tools (e.g., REBUS, needle, forceps) intra-operatively in real-time. This can enable application of different computer assisted techniques, such as augmented reality and image overlays in camera images in order to improve guidance of the tools and clinical outcomes. One example can include integrating endoscopic ultrasound or other imaging information with the camera images based on the detected tool positions. Tool pose estimation can also be used to provide dynamic motion constraints or detect tool-tissue interactions (for providing force feedback for example).

In some embodiments, the workflow recognition system can incorporate robotic instruments with radio-frequency identification (RFID tags), which can allow the system to identify each of the tools (REBUS, Needle, Forceps) through such tags. Tools may be tracked through position sensor information coming from the tools, combined with the kinematic information of the robot. Electromagnetic (EM) and robot kinematic data obtained from the robotic platform can be used together with the machine learning framework for extracting workflow (phase/activity) and skill information, prior to the targeting phase. Other position sensors (e.g. shape sensing) can be used for such purpose as well.

Example Robotic System

FIG. 8 illustrates example details of a robotic system 110 that can incorporate the automated tool detection system, according to certain embodiments. In this example, the robotic system 110 is illustrated as a cart-based robotically-enabled system that is movable. However, the robotic system 110 can be implemented as a stationary system, integrated into a table, and so on. The automated tool detection system can be implemented as a module of the robotic system 110.

The robotic system 110 can include the support structure 114 including an elongated section 114(A) (sometimes referred to as "the column 114(A)") and a base 114(B). The column 114(A) can include one or more carriages, such as a carriage 1102 (alternatively referred to as "the arm support 1102") for supporting the deployment of one or more the robotic arms 112 (three shown in FIG. 8). The carriage 1102 can include individually configurable arm mounts that rotate along a perpendicular axis to adjust the base of the robotic arms 112 for positioning relative to a patient. The carriage 1102 also includes a carriage interface 1104 that allows the carriage 1102 to vertically translate along the column 114 (A). The carriage interface 1104 is connected to the column 114(A) through slots, such as slot 1106, that are positioned on opposite sides of the column 114(A) to guide the vertical translation of the carriage 1102. The slot 1106 includes a vertical translation interface to position and hold the carriage 1102 at various vertical heights relative to the base 114(B). Vertical translation of the carriage 1102 allows the robotic system 110 to adjust the reach of the robotic arms 112 to meet a variety of table heights, patient sizes, physician preferences. etc. Similarly, the individually configurable arm mounts on the carriage 1102 allow a robotic arm base 1108 of the robotic arms 112 to be angled in a variety of configurations. The column 114(A) can internally comprise mechanisms, such as gears and/or motors, that are designed to use a vertically aligned lead screw to translate the carriage 1102 in a mechanized fashion in response to control signals generated in response to user inputs, such as inputs from the I/O device(s) 116.

In some embodiments, the slot 1106 can be supplemented with a slot cover(s) that is flush and/or parallel to the slot surface to prevent dirt and/or fluid ingress into the internal chambers of the column 114(A) and/or the vertical translation interface as the carriage 1102 vertically translates. The slot covers can be deployed through pairs of spring spools positioned near the vertical top and bottom of the slot 1106. The covers can be coiled within the spools until deployed to extend and retract from their coiled state as the carriage 1102 vertically translates up and down. The spring-loading of the spools can provide force to retract the cover into a spool when the carriage 1102 translates towards the spool, while also maintaining a tight seal when the carriage 1102 translates away from the spool. The covers can be connected to the carriage 1102 using, for example, brackets in the carriage interface 1104 to ensure proper extension and retraction of the covers as the carriage 1102 translates.

The base 114(B) can balance the weight of the column 114(A), the carriage 1102, and/or arms 112 over a surface, such as the floor. Accordingly, the base 114(B) can house heavier components, such as one or more electronics, motors, power supply, etc., as well as components that enable movement and/or immobilize the robotic system 110. For example, the base 114(B) can include rollable wheels 1116 (also referred to as "the casters 1116") that allow for the robotic system 110 to move around the room for a procedure. After reaching an appropriate position, the casters 1116 can be immobilized using wheel locks to hold the robotic system 110 in place during the procedure. As shown, the robotic system 110 also includes a handle 1118 to assist with maneuvering and/or stabilizing the robotic system 110.

The robotic arms 112 can generally comprise robotic arm bases 1108 and end effectors 1110, separated by a series of linkages 1112 that are connected by a series of joints 1114. Each joint 1114 can comprise an independent actuator and each actuator can comprise an independently controllable motor. Each independently controllable joint 1114 represents an independent degree of freedom available to the robotic arm 112. For example, each of the arms 112 can have seven joints, and thus, provide seven degrees of freedom. However, any number of joints can be implemented with any degrees of freedom. In examples, a multitude of joints can result in a multitude of degrees of freedom, allowing for "redundant" degrees of freedom. Redundant degrees of freedom allow the robotic arms 112 to position their respective end effectors 1110 at a specific position, orientation, and/or trajectory in space using different linkage positions and/or joint angles. In some embodiments, the end effectors 1110 can be configured to engage with and/or control a medical instrument, a device, an object, and so on. The freedom of movement of the arms 112 can allow the robotic system 110 to position and/or direct a medical instrument from a desired point in space and/or allow a physician to move the arms 112 into a clinically advantageous position away from the patient to create access, while avoiding arm collisions.

As shown in FIG. 8, the robotic system 110 can also include the I/O device(s) 116. The I/O device(s) 116 can include a display, a touchscreen, a touchpad, a projector, a mouse, a keyboard, a microphone, a speaker, a controller, a camera (e.g., to receive gesture input), or another I/O device to receive input and/or provide output. The I/O device(s) 116 can be configured to receive touch, speech, gesture, or any other type of input. The I/O device(s) 116 can be positioned at the vertical end of column 114(A) (e.g., the top of the column 114(A)) and/or provide a user interface for receiving user input and/or for providing output. For example, the I/O device(s) 116 can include a touchscreen (e.g., a dual-purpose device) to receive input and provide a physician with pre-operative and/or intra-operative data. Example pre-operative data can include pre-operative plans, navigation, and/or mapping data derived from pre-operative computerized tomography (CT) scans, and/or notes from pre-operative patient interviews. Example intra-operative data can include optical information provided from a tool/instrument, sensor, and/or coordinate information from sensors, as well as vital patient statistics, such as respiration, heart rate, and/or pulse. The I/O device(s) 116 can be positioned and/or tilted to allow a physician to access the I/O device(s) 116 from a variety of positions, such as the side of the column 114(A) opposite the carriage 1102. From this position, the physician can view the I/O device(s) 116, the robotic arms 112, and/or a patient while operating the I/O device(s) 116 from behind the robotic system 110.

The robotic system 110 can include a variety of other components. For example, the robotic system 110 can include one or more control electronics/circuitry, power sources, pneumatics, optical sources, actuators (e.g., motors to move the robotic arms 112), memory, and/or communication interfaces (e.g. to communicate with another device). In some embodiments, the memory can store computer-executable instructions that, when executed by the control circuitry, cause the control circuitry to perform any of the operations discussed herein. For example, the memory can store computer-executable instructions that, when executed by the control circuitry, cause the control circuitry to receive input and/or a control signal regarding manipulation of the robotic arms 112 and, in response, control the robotic arms 112 to be positioned in a particular arrangement and/or to navigate a medical instrument connected to the end effectors 1110.

In some embodiments, robotic system 110 is configured to engage with and/or control a medical instrument. For example, the robotic arms 112 can be configured to control a position, orientation, and/or tip articulation of a scope (e.g., a sheath and/or a leader of the scope). Alternatively, or in combination, the robotic arms 112 can be configured to control a position, orientation, and/or tip actuation of a working channel instrument inserted through the scope. In some embodiments, one or more instruments such as a working channel instrument can be controlled manually. As further described herein, images can be obtained by a video capture device of the system and used to facilitate tool, workflow, phase, and/or activity recognition. For example, in some embodiments, video obtained by the scope can include video of working channel instruments (e.g., REBUS, needle, forceps, biopsy instrument, etc.) inserted through the scope, and such video can be used to identify the working channel instrument. In some embodiments, the robotic arms 112 can be configured/configurable to manipulate the scope using elongate movement members. The elongate movement members can include one or more pull wires (e.g., pull or push wires), cables, fibers, and/or flexible shafts. To illustrate, the robotic arms 112 can be configured to actuate multiple pull wires coupled to the scope to deflect the tip of the scope. Pull wires can include any suitable or desirable materials, such as metallic and/or non-metallic materials such as stainless steel, Kevlar, tungsten, carbon fiber, and the like. In some embodiments, the scope is configured to exhibit nonlinear behavior in response to forces applied by the elongate movement members. The nonlinear behavior can be based on stiffness and compressibility of the scope, as well as variability in slack or stiffness between different elongate movement members.

Example Control System

Figure 9:
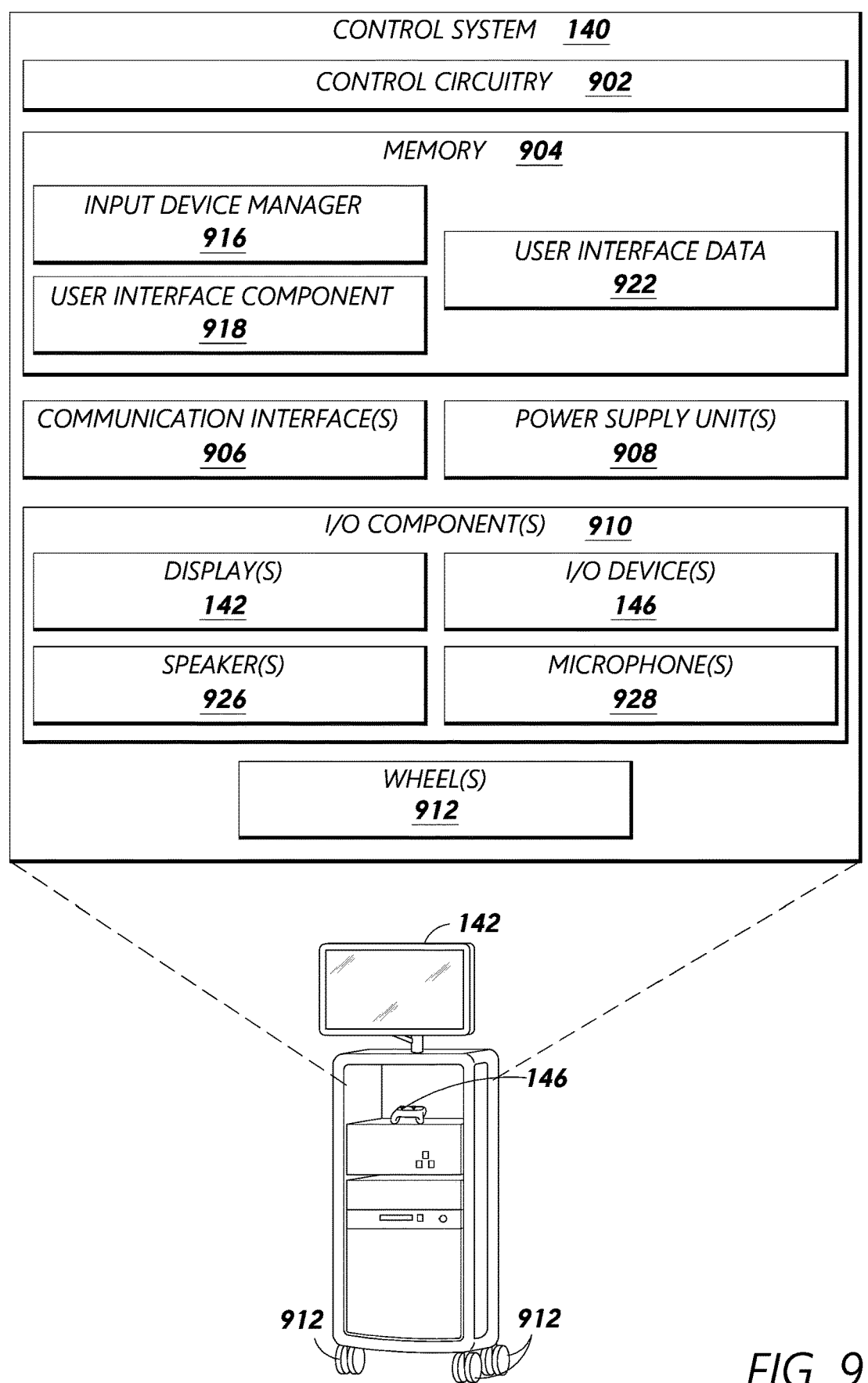
FIG. 9 illustrates example details of the control system of the robotic system, according to certain embodiments.

FIG. 9 illustrates example details of the control system 140 in accordance with one or more embodiments. As illustrated, the control system 140 can include one or more of the following components, devices, modules, and/or units (referred to herein as "components"), either separately/individually and/or in combination/collectively: control circuitry 902, data storage/memory 904, one or more communication interfaces 906, one or more power supply units 908, one or more I/O components 910, and/or one or more wheels 912 (e.g., casters or other types of wheels). In some embodiments, the control system 140 can comprise a housing/enclosure configured and/or dimensioned to house or contain at least part of one or more of the components of the control system 140. In this example, the control system 140 is illustrated as a cart-based system that is movable with the one or more wheels 912. In some cases, after reaching the appropriate position, the one or more wheels 912 can be immobilized using wheel locks to hold the control system 140 in place. However, the control system 140 can be implemented as a stationary system, integrated into another system/device, and so on.

Although certain components of the control system 140 are illustrated in FIG. 9, it should be understood that additional components not shown can be included in embodiments in accordance with the present disclosure. Furthermore, certain of the illustrated components can be omitted in some embodiments. Although the control circuitry 902 is illustrated as a separate component in the diagram of FIG. 9, it should be understood that any or all of the remaining components of the control system 140 can be embodied at least in part in the control circuitry 902. That is, the control circuitry 902 can include various devices (active and/or passive), semiconductor materials and/or areas, layers, regions, and/or portions thereof, conductors, leads, vias, connections, and/or the like, wherein one or more of the other components of the control system 140 and/or portion(s) thereof can be formed and/or embodied at least in part in/by such circuitry components/devices.

The various components of the control system 140 can be electrically and/or communicatively coupled using certain connectivity circuitry/devices/features, which can or may not be part of the control circuitry 902. For example, the connectivity feature(s) can include one or more printed circuit boards configured to facilitate mounting and/or interconnectivity of at least some of the various components/circuitry of the control system 140. In some embodiments, two or more of the control circuitry 902, the data storage/memory 904, the communication interface(s) 906, the power supply unit(s) 908, and/or the input/output (I/O) component(s) 910, can be electrically and/or communicatively coupled to each other.

As illustrated, the memory 904 can include an input device manager 916 and a user interface (UI) component 918 configured to facilitate various functionality discussed herein. In some embodiments, the input device manager 916, and/or the user interface component 918 can include one or more instructions that are executable by the control circuitry 902 to perform one or more operations. Although many embodiments are discussed in the context of the components 916-918 including one or more instructions that are executable by the control circuitry 902, any of the components 916-918 can be implemented at least in part as one or more hardware logic components, such as one or more application specific integrated circuits (ASIC), one or more field-programmable gate arrays (FPGAs), one or more application-specific standard products (ASSPs), one or more complex programmable logic devices (CPLDs), and/or the like. Furthermore, although the components 916-918 are illustrated as being included within the control system 140, any of the components 916-918 can be implemented at least in part within another device/system, such as the robotic system 110, the table 150, or another device/system. Similarly, any of the other components of the control system 140 can be implemented at least in part within another device/system.

The input device manager 1216 can be configured to receive inputs from the input device 146 and translate them into actions performable by the robotic system 110. For example, pre-programmed motions, such as open, close, jiggle motion, and other commands for particular instruments can be stored in the input device manager 1216. These pre-programmed motions can then be assigned to the desired input (e.g., single or dual button presses, voice commands, joystick movements, etc.). In some implementations, the pre-programmed motions are determined by the manufacturer. In other implementations, users may be able to modify existing pre-programmed motions and/or create new ones. For motions that are associated with specific instruments, data (e.g., triggered motion, time of activation, associated instrument, etc.) on the triggering of these motions can be used as supplemental data to help identify tracked instruments in video that is being analyzed.

The user interface component 1918 can be configured to facilitate one or more user interfaces (also referred to as "one or more graphical user interfaces (GUI)"). For example, the user interface component 1918 can generate a configuration menu for assigning pre-programmed motions to inputs or a settings menu for enabling certain modes of operation or disabling selected pre-programmed motions in specific situations. The user interface component 918 can also provide user interface data 922 for display to the user.

The one or more communication interfaces 906 can be configured to communicate with one or more device/sensors/systems. For example, the one or more communication interfaces 906 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 906 can implement a wireless technology such as Bluetooth, Wi-Fi, near field communication (NFC), or the like.

The one or more power supply units 908 can be configured to manage power for the control system 140 (and/or the robotic system 110, in some cases). In some embodiments, the one or more power supply units 908 include one or more batteries, such as a lithium-based battery, a lead-acid battery, an alkaline battery, and/or another type of battery. That is, the one or more power supply units 908 can comprise one or more devices and/or circuitry configured to provide a source of power and/or provide power management functionality. Moreover, in some embodiments the one or more power supply units 908 include a mains power connector that is configured to couple to an alternating current (AC) or direct current (DC) mains power source.

The one or more I/O components 910 can include a variety of components to receive input and/or provide output, such as to interface with a user. The one or more I/O components 910 can be configured to receive touch, speech, gesture, or any other type of input. In examples, the one or more I/O components 910 can be used to provide input regarding control of a device/system, such as to control the robotic system 110, navigate the scope or other medical instrument attached to the robotic system 110, control the table 150, control the fluoroscopy device 190, and so on. As shown, the one or more I/O components 910 can include the one or more displays 142 (sometimes referred to as "the one or more display devices 142") configured to display data. The one or more displays 142 can include one or more liquid-crystal displays (LCD), light-emitting diode (LED) displays, organic LED displays, plasma displays, electronic paper displays, and/or any other type(s) of technology. In some embodiments, the one or more displays 142 include one or more touchscreens configured to receive input and/or display data. Further, the one or more I/O components 910 can include the one or more input devices 146, which can include a touchscreen, touch pad, controller, mouse, keyboard, wearable device (e.g., optical head-mounted display), virtual or augmented reality device (e.g., head-mounted display), etc. Additionally, the one or more I/O components 910 can include one or more speakers 926 configured to output sounds based on audio signals and/or one or more microphones 928 configured to receive sounds and generate audio signals. In some embodiments, the one or more I/O components 910 include or are implemented as a console.

Although not shown in FIG. 9, the control system 140 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and aspiration capabilities can be delivered directly to a medical instrument through separate cable(s). Further, the control system 140 can include a voltage and/or surge protector designed to provide filtered and/or protected electrical power to another device, such as the robotic system 110, thereby avoiding placement of a power transformer and other auxiliary power components in robotic system 110, resulting in a smaller, more moveable robotic system 110.

The control system 140 can also include support equipment for sensors deployed throughout the robotic system 110. For example, the control system 140 can include opto-electronics equipment for detecting, receiving, and/or processing data received from optical sensors and/or cameras. Such opto-electronics equipment can be used to generate real-time images for display in any number of devices/systems, including in the control system 140.

In some embodiments, the control system 140 can be coupled to the robotic system 110, the table 150, and/or a medical instrument, such as the scope, through one or more cables or connections (not shown). In some implementations, support functionality from the control system 140 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Phase Recognition

Automated surgical workflow analysis can be used to detect different phases in a procedure and to assess surgical skill and procedural efficiency. Data collected during procedures (e.g. video data) can be segmented into multiple sections using, for example, machine learning methods, including but not limited to, a hidden Markov model (HMM), a long-term-short-memory (LTSM) network, and the other machine learning algorithms discussed above.

In surgical phase segmentation, captured medical procedure data is automatically segmented into phases, using input data from the operating room to identify the phases. Segmentation may be done in real-time during the procedure or performed post-operatively on recorded data. In one embodiment, the surgical data can be preprocessed using dynamic time warping to divide the phases into equal comparable segments. The input data can consist of instrument signals, annotations, tracking of instruments (e.g. EM), other supplemental data from the robotic system 110, and/or information obtained from videos.

Figures 10, 11A, 11B:
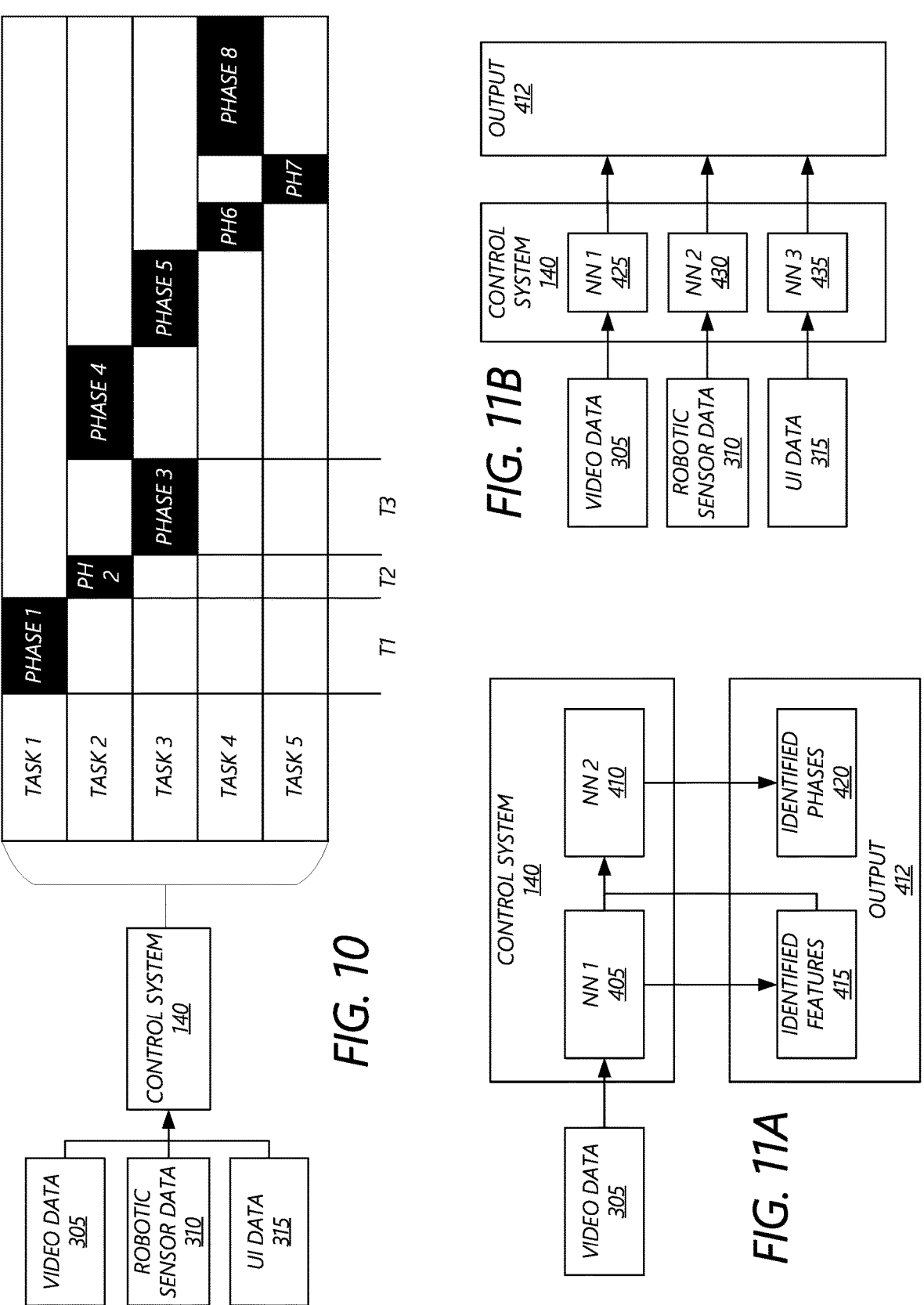
FIG. 10 illustrates a block diagram of the control system, with associated inputs and outputs, according to certain embodiments.
FIG. 11A illustrates a block diagram of the control system configured to utilize machine learning to generate outputs from video data, according to certain embodiments.
FIG. 11B illustrates a block diagram of the control system configured to utilize machine learning to generate outputs from several types of data, according to certain embodiments.

Recognition of surgical workflow can be done at different granularity levels, depending on the procedure. It can be done on phases and steps (higher level), or gestures and activities (lower level). Surgical phase recognition can be performed on time series, kinematic data, and video data using machine learning approaches such as HMMs, Gaussian Mixture Models (GMMs), and Support Vector Machines (SVMs), as well as deep learning-based approaches for phase recognition from video data using Convolutional Neural Networks (CNNs) and the other machine learning algorithms discussed above. For surgical gesture and activity recognition similar methods (SVMs, Markov models) can be used on mainly video data or a combination of video and kinematic data, as well as more recent deep-learning based methods such as CNNs and other machine learning algorithms can be used for recognition of tool presence, tasks, and activities in video data. Phase segmentation can use multiple data sources to segment the case data to different subtasks as shown in FIG. 10 or use a single data source, such as video, to classify the current phase as shown in FIG. 11A. In FIG. 11B, additional data (e.g. sensor data or UI data) can then be incorporated to further refine the output produced by the control system 140.

In FIG. 10, the control system 140 receives various input data from the robotic system 110. Such input can include video data 305 captured by the imaging sensor 180, robotic sensor data 310 from one or more sensors of the robotic system 110, and user interface (UI) data received from the input device 146.

Video data 305 can include video captured from scopes deployed within a patient, video captured from cameras in the operating room, and/or video captured by cameras of the robotic system 110. Robotic sensor data 310 can include kinematic data from the robotic system 110 (e.g., using vibration, accelerometer, positioning, and/or gyroscopic sensors), device status, temperature, pressure, vibration, haptic/tactile features, sound, optical levels or characteristics, load or weight, flow rate (e.g., of target gases and/or liquid), amplitude, phase, and/or orientation of magnetic and electronic fields, constituent concentrations relating to substances in gaseous, liquid, or solid form, and/or the like. UI data 315 can include button presses, menu selections, page selections, gestures, voice commands, and/or the like made by the user and captured by input devices of the robotic system 110. Patient sensor data may also be used as an input to the control system 140.

The control system 140 can analyze the video data 305 (e.g., using machine learning algorithms), as well as using robotic sensor data 310 and UI data 315 to identify phases of the a medical procedure. In one example, a medical procedure such as bronchoscopy includes several tasks (e.g., Task 1-Task 5). Each task may be performed in one or more phases of the medical procedure. In the example shown in FIG. 10, Task 1 is performed in phase 1. Task 2 is performed in phase 2 and 4. Task 3 is performed in phase 3 and phase 5. Task 4 is performed din phase 6 and 8. Task 5 is performed in phase 7. Time 1 (T1) denotes the time taken to complete phase 1, Time 2 (T2) denotes the time taken to complete phase 2, and time 3 (T3) denotes the time taken to complete phase 3. Other procedures may have a different number of tasks and/or a different number of phases.

For robotic procedures where there are manual and automated task, surgical phase detection can be used to make the transition between manual and automated tasks automatic and seamless. For example, T1 may correspond to a manual task, T2 may be an automated task, and T3 may again be a manual task. In one embodiment, when the target selection phase is active, the target selection step can be autonomously performed by the robot driving the scope. Alternatively, the user can perform site selection by picking a point on the skin using an EM marker, and the robot can autonomously align the needle to the target insertion trajectory.

FIG. 11A illustrates a block diagram of the control system 140 configured to utilize machine learning to generate outputs from video data from a medical procedure, according to certain embodiments. In some embodiments, the control system 140 is configured to process the video data 305 first, using machine learning algorithms such as those described earlier. In one embodiment, video data 305 is processed by a first neural network 405 to generate output 412 to identify features recorded in the video, such as surgical tools, stone(s), human anatomy (e.g., papilla), or the like. Such identified features 415 may be provided as input to a second neural network 410, along with the original video. The second neural network 410 can then process the video data 305 and the identified features 415 to generate output 412 to identify phases 420 in a medical procedure. Other embodiments may use more neural networks or combine neural networks (e.g. multi-stage architectures).

Supplemental data such as robotic sensor data 310 or UI data 315 may then be used to further refine (e.g., increase accuracy or increase the number of identifications) the identified features 415 and the identified phases 420. In other embodiments, the robotic sensor data 310 and/or UI data 315 can be used prior to the processing of the video data 305 by the control system 140 to narrow the possible options considered by the control system 140. For example, the supplemental data can be used to identify a specific procedure, which narrows the universe of possible tasks and phases to those corresponding to the specific procedure. The control system 140 may then limit the identified features 415 and identified phases 420 to those that correspond to the specific procedure. For example, if a task is initially identified in the video data 305 by the control system 140, but that task is not associated with the specific procedure, the control system 140 may reprocess the video until the task is re-identified as a task corresponding to the specific procedure.

After completing processing of the video data 305, the control system 140 may generate an annotated video that includes the identified features 415 and/or identified phases 420. Such annotations may be stored as part of the video (e.g., in the same video file), meta-data stored alongside the video, in a database, and/or other data format.

By creating meta-data enhanced video, the video becomes easier to use for reviewing medical procedures. For example, a viewer can jump forward or backward to specific phase of interest rather than manually searching for when a specific phase occurred. In addition, multiple videos can be more easily processed to aggregate data and generate metrics. For example, multiple videos can be searched for instances of a particular phase (e.g., needle insertion or stone capture), and analyzed to generate metrics about the that phase (e.g., success rates, average attempts, number of attempts, etc.).

While FIG. 11A shows video data 305 being processed by the control system 140, other types of data can be processed by the control system 140, serially or in tandem with each other. For example, such data can include instrument positioning as measure by electromagnetic tracking sensors, robotic system 110 data such as how far the scope is inserted, how the scope is articulated, if an instrument is open or closed, how far the instrument is inserted, and/or the connection status of the robotic system. The data can be provided as input to a single neural network or to multiple neural networks. For example, each different type of sensor (e.g., video, device status, telemetry such as: magnetic tracking; robot data; and/or fluidics data) may have its own network and the outputs of the networks may be concatenated before the final phase classification layer to obtain a single phase prediction.

FIG. 11B illustrates one such embodiment where different types of data from different devices and/or sensors are processed by different neural networks. Video data 305 can be processed by a first neural network 425, robotic sensor data 310 can be processed by a second neural network 430, and UI data can be processed by a third neural network 435. The outputs from the different neural networks may then be combined to generate an output 412 (e.g., phase prediction) for the robotic system 110.

Instrument Identification

Figure 12:
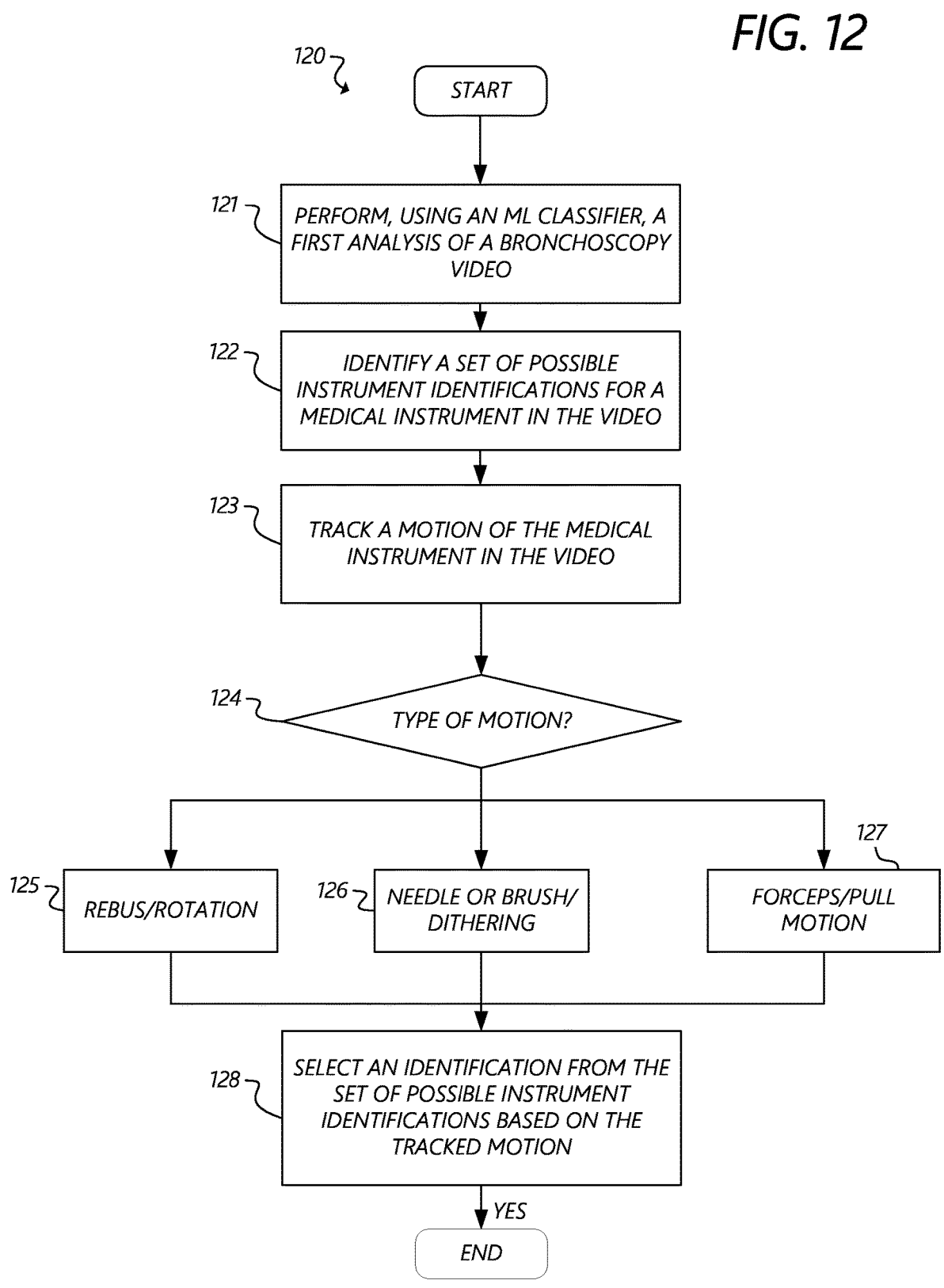
FIG. 12 is a flow diagram of an instrument identification process, according to certain embodiments.

FIG. 12 is a flow diagram of an instrument identification process 120, according to certain embodiments. The phase identification process 130 can be performed by the automated tool detection system, which may be implemented by the control system 140 or by another component of the robotic system 110. Selection data used by the control system 140, such as types of motions, types of medical instruments used during particular phases, coloring of certain medical instruments, and/or the like can be stored in the memory 904 of the robotic system 110 (FIG. 9). In addition, while the above has discussed the process 120 in terms of the robotic system 110, the phase identification process 130 may also be performed by a stand-alone computing system, separate from the robotic system 110. For example, the process 120 may be performed as a post-operative analysis of recorded medical procedures videos. Furthermore, while the following describes one possible sequence to the process, other embodiments can perform the process in a different order or may include additional steps or may exclude one or more of the steps described below.

At block 121, the control system 140 performs a first analysis of a bronchoscopy video. The first analysis can be performed by a machine learning classifier such as those described earlier. The first analysis may include one or more of a phase recognition step, a tool-presence detection step, and/or an episode recognition step.

At block 122, the control system 140 identifies a set of possible instrument identifications for a medical instrument in the video. As discussed above, supplemental data such as robotic sensor data or UI data may then be used to further narrow the possibilities. For example, the supplemental data can be used to identify a specific phase of the bronchoscopy procedure, which narrows the universe of possible tasks and phases to those corresponding to the specific phase.

In one example, the bronchoscopy procedure may include multiple phases, with different tools and actions more likely to be used in one phase than the others. The control system 140 may then filter out some possible instrument identifications to those that correspond to the specific phase. For example, during an earlier phase, a tracked medical instrument may be more likely to be a sheath than a forceps, which is used during a later phase to obtain a sample. In some embodiments, depending on whether the medical instrument appears during the a phase or a second phase, different sets of possible classifications may be used to filter the possible instrument identifications.

In one embodiment, the control system 140 may use the first appearance of a medical instrument to delineate one phase from another. In some embodiments, the robotic system 110 uses a bronchoscope with both a working channel for tool insertion and an integrated camera. This allows the robotic system to capture images of working channel tools during phases of the procedure. Those captured images may then be used to automatically recognize phases of a bronchoscopy procedure.

In one scenario, during the navigation phase, no medical instrument other than the bronchoscope is being used, so video captured by the bronchoscope at this time will show no other instruments and/or a background (e.g., bronchial lumens). When the target site is reached, additional instruments are deployed through, for example, the working channel of the bronchoscope. In some embodiments, the control system can use the first appearance of a first medical instrument to record a timestamp (e.g., time 5:05 in the video) indicating a change in the phase of the medical procedure. A first time period before the timestamp may be designated the navigation phase while a second time period after the timestamp may be designated the targeting phase. The first time period before the timestamp can be inclusive of the timestamp, with the second period occurring subsequent to the first time period. In some embodiments, the second period after the timestamp can be inclusive of the timestamp.

The control system 140 may aggregate data on the navigation phase and the targeting phase across multiple procedures across various criteria (e.g., multiple bronchoscopy procedures by the same robotic system, multiple procedures by the same user or medical team, multiple procedures by location of target site, etc.). Some embodiments may aggregate data for additional phases of the procedure. With the aggregated data, the control system 140 can generate statistics for the procedures. In one example, the control system 140 can determine a first average time for the navigation phase and a second average time for the targeting phase. Such information may be useful in evaluating medical teams and/or planning out future procedures.

At block 123, the control system 140 tracks a motion of the medical instrument in the video. The motion may be processed by the machine learning classifier to identify the type of motion.

At block 124, the control system 140 determines the type of motion. Certain types of motions can be associated with certain classes of instruments, each class of which may include one or more instrument identifications. During bronchoscopy, certain instruments are more likely to be used in certain ways than others. For example, a brush may be moved back and forth to remove debris, a forceps may be quickly pulled back to retrieve a sample, a needle tip may be moved back and forth to obtain a tissue from a sampling location.

At block 125, if the type of motion is a rotation motion, the medical instrument can be identified as a REBUS. At block 126, if the type of motion is a dithering or back and forth motion, the medical instrument can be identified as a needle or brush. In situations where multiple instruments share the same motion, supplemental data, such as color of the instrument, can be used to further distinguishing between the two instruments. At block 127, if the type of motion is a pulling motion, which may be a quick and hard pull, the medical instrument can be identified as a forceps. Other types of motions may be associated with other medical instruments.

At block 128, the control system 140 selects an identification from the set of possible instrument identifications based on the tracked motion. Other types of supplemental data from the robotic system 110 may also be used to aid in the identification. For example, the sensors in the robotic arm can indicate how the robotic arm is moving during a particular time corresponding to the bronchoscopy video. This information can be used to more easily identify the type of motion recorded in the bronchoscopy video. In another example, as discussed earlier, the color of the instrument can be used to distinguish between a brush or a needle. In another example, UI selections by the user can help indicate the task being performed at particular times (e.g., using timestamps). These tasks times can be used to narrow down the possibly instruments being used. After the identification is made, the control system 140 can record the identification as metadata for the video or separately in a database, electronic document, or other data storage. The process 120 can then end.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A robotic system for automatically identifying surgical instruments used during a bronchoscopy procedure, the robotic system comprising:

a video capture device;

a robotic manipulator;

one or more sensors configured to detect a configuration of the robotic manipulator;

control circuitry communicatively coupled to the robotic manipulator, the control circuitry configured to:

perform, using a machine learning classifier, a first analysis of a bronchoscopy video of a patient site captured by the video capture device, the first analysis configured to categorize a medical instrument in the bronchoscopy video into a first tool class of a plurality of tool classes;

identify a set of possible instrument types for the medical instrument in the bronchoscopy video based on the first tool class and an identified phase of the bronchoscopy procedure, wherein the set of possible instrument types includes one or more phase-specific medical instruments that are associated with the first tool class and known to be employed for the identified phase;

track a motion of the medical instrument in the bronchoscopy video; and select a type of instrument from the set of possible instrument types for the medical instrument based at least in part on the tracked motion.

2. The robotic system of claim 1, wherein the tracked motion comprises a rotation of the medical instrument and the type of instrument is a radial probe endobronchial ultrasound (REBUS) instrument.

3. The robotic system of claim 1, wherein the tracked motion comprises a pull motion of the medical instrument and the type of instrument is a forceps.

4. The robotic system of claim 1, wherein the tracked motion comprises a back and forth dithering motion of the medical instrument and the type of instrument is a needle or a brush.

5. The robotic system of claim 4, wherein a color of the medical instrument is used to further identify the medical instrument as the needle.

6. The robotic system of claim 1, wherein the plurality of tool classes comprises at least a sheath class, a needle class, a REBUS class, a forceps class, a brush class, and a background class.

7. The robotic system of claim 1, wherein the plurality of tool classes comprises at least a sheath class and a needle class.

8. The robotic system of claim 7, wherein the sheath class comprises medical instruments including a REBUS, a needle, and a forceps.

9. The robotic system of claim 7, wherein the needle class comprises medical instruments including a needle tip, a brush, or a sheath.

10. The robotic system of claim 1, wherein the control circuitry is further configured to identify a phase of the bronchoscopy procedure based at least in part on sensor data from the one or more sensors.

11. A method for automatically identifying surgical instruments used during a bronchoscopy procedure by a robotic system, the method comprising:

performing, using a machine learning classifier, a first analysis of a bronchoscopy video of a patient site captured by a video capture device of the robotic system, the first analysis configured to categorize a medical instrument in the bronchoscopy video into a first tool class of a plurality of tool classes;

identifying a set of possible instrument types for the medical instrument in the bronchoscopy video based on the first tool class and an identified phase of the bronchoscopy procedure, wherein the set of possible instrument types includes one or more phase-specific medical instruments associated with the first tool class and known to be employed for the identified phase;

tracking a motion of the medical instrument in the bronchoscopy video; and selecting a type of instrument from the set of possible instrument types for the medical instrument based at least in part on the tracked motion.

12. The method of claim 11, wherein the tracked motion comprises a rotation of the medical instrument and the type of instrument is a radial probe endobronchial ultrasound (REBUS) instrument.

13. The method of claim 11, wherein the tracked motion comprises a pull motion of the medical instrument and the type of instrument is a forceps.

14. The method of claim 11, wherein the tracked motion comprises a back and forth dithering motion of the medical instrument and the type of instrument is a needle or a brush.

15. The method of claim 11, further comprising:

identifying the phase of the bronchoscopy procedure based at least in part on sensor data from the robotic system.

16. The method of claim 11, wherein the plurality of classes comprise at least a REBUS class, a forceps class, a brush class, and a background class.

17. The method of claim 11, wherein the machine learning classifier is further configured to perform an episode recognition process.

18. The method of claim 17, wherein the episode recognition process comprises classifying the medical instrument into one of several classes based at least in part on the tracked motion.

19. A computerized system for automatically identifying surgical instruments used during a bronchoscopy procedure, the computerized system comprising:

one or more processors configured to:

perform, using a machine learning classifier, a first analysis of a bronchoscopy video of a patient site captured by a video capture device, the first analysis configured to categorize a medical instrument in the bronchoscopy video into a first tool class of a plurality of tool classes;

identify a set of possible instrument types for the medical instrument in the bronchoscopy video based on the first tool class and an identified phase of the bronchoscopy procedure, wherein the set of possible instrument types includes one or more phase-specific medical instruments associated with the first tool class and known to be employed for the identified phase;

track a motion of the medical instrument in the bronchoscopy video; and select a type of instrument from the set of possible instrument types for the medical instrument based at least in part on the tracked motion.

* * * * *